US010987177B2

(12) United States Patent
Overmyer et al.

(10) Patent No.: US 10,987,177 B2
(45) Date of Patent: Apr. 27, 2021

(54) ROBOTIC ENDOCUTTER DRIVETRAIN WITH BAILOUT AND MANUAL OPENING

(71) Applicant: Ethicon LLC, Guaynabo, PR (US)

(72) Inventors: Mark D. Overmyer, Cincinnati, OH (US); Jeffrey S. Swayze, Hamilton, OH (US); Robert L. Koch, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 658 days.

(21) Appl. No.: 15/385,025

(22) Filed: Dec. 20, 2016

(65) Prior Publication Data

US 2018/0168745 A1    Jun. 21, 2018

(51) Int. Cl.
*A61B 34/30* (2016.01)
*A61B 17/072* (2006.01)
(Continued)

(52) U.S. Cl.
CPC ........ *A61B 34/30* (2016.02); *A61B 17/07207* (2013.01); *A61B 17/29* (2013.01);
(Continued)

(58) Field of Classification Search
CPC . A61B 34/30; A61B 17/07207; A61B 17/072; A61B 17/068; A61B 2017/00398;
(Continued)

(56) References Cited

U.S. PATENT DOCUMENTS 8,114,345 B2    2/2012 Dlugos, Jr. et al.
8,292,150 B2 * 10/2012 Bryant ................ A61B 17/068
227/175.1
(Continued)

FOREIGN PATENT DOCUMENTS

EP    2803324 A2    11/2014
EP    2992838 A2    3/2016
(Continued)

OTHER PUBLICATIONS

U.S. Appl. No. 15/385,028, filed Dec. 20, 2016, Mark D. Overmyer et al.
(Continued)

*Primary Examiner* — Anna K Kinsaul
*Assistant Examiner* — Veronica Martin
(74) *Attorney, Agent, or Firm* — Mintz Levin Cohn Ferris Glovsky and Popeo, P.C.

(57) ABSTRACT

Various embodiments of tool assemblies are provided having at least one rotary input coupling and at least one linear input coupling for allowing either a rotary output or a linear output (e.g., from a tool driver on a surgical robot) to activate at least one mechanism of the tool assembly. For example, mechanisms of the tool assembly can include a clamping assembly, a firing assembly, an articulation assembly, and a roll assembly. The clamping assembly can open and close jaws of an end effector, the firing assembly can translate a knife assembly through the end effector to fire staples and cut tissue, the articulation assembly can articulate the end effector, and the roll assembly can rotate the elongate shaft and/or the end effector.

26 Claims, 16 Drawing Sheets

(51) Int. Cl.
*A61B 17/29* (2006.01)
*A61B 17/00* (2006.01)

(52) U.S. Cl.
CPC ............... *A61B 2017/00393* (2013.01); *A61B 2017/00398* (2013.01); *A61B 2017/00407* (2013.01); *A61B 2017/00477* (2013.01); *A61B 2017/00982* (2013.01); *A61B 2017/07285* (2013.01); *A61B 2017/2903* (2013.01); *A61B 2017/2923* (2013.01); *A61B 2017/2927* (2013.01); *A61B 2017/2943* (2013.01); *A61B 2034/302* (2016.02)

(58) Field of Classification Search
CPC ........... A61B 2017/00393; A61B 2017/00407; A61B 2017/00477; A61B 2017/00982; A61B 2017/07285; A61B 2017/2903; A61B 2017/2923; A61B 2017/2927; A61B 2017/2943
USPC ....................................................... 227/175
See application file for complete search history.

(56) References Cited

U.S. PATENT DOCUMENTS

| | | | |
|---|---|---|---|
| 8,876,857 B2 | 11/2014 | Burbank | |
| 9,039,720 B2 | 5/2015 | Madan | |
| 9,386,984 B2 | 7/2016 | Aronhalt et al. | |
| 2003/0130677 A1* | 7/2003 | Whitman | A61B 17/072 606/167 |
| 2007/0023476 A1* | 2/2007 | Whitman | A61B 17/072 227/175.1 |
| 2008/0255413 A1* | 10/2008 | Zemlok | A61B 17/072 600/106 |
| 2009/0057369 A1 | 3/2009 | Smith et al. | |
| 2010/0089970 A1* | 4/2010 | Smith | A61B 17/07207 227/175.1 |
| 2011/0295269 A1* | 12/2011 | Swensgard | A61B 17/068 606/130 |
| 2012/0132450 A1* | 5/2012 | Timm | A61B 17/072 173/47 |
| 2012/0181322 A1* | 7/2012 | Whitman | A61B 17/07207 227/176.1 |
| 2012/0199632 A1* | 8/2012 | Spivey | A61B 17/07207 227/176.1 |
| 2013/0334278 A1* | 12/2013 | Kerr | A61B 17/07207 227/175.1 |
| 2014/0001235 A1* | 1/2014 | Shelton, IV | A61B 17/07207 227/176.1 |
| 2014/0005678 A1 | 1/2014 | Shelton, IV et al. | |
| 2014/0014707 A1 | 1/2014 | Onukuri et al. | |
| 2014/0224856 A1 | 8/2014 | Smith et al. | |
| 2014/0263541 A1* | 9/2014 | Leimbach | A61B 17/0686 227/175.2 |
| 2015/0173789 A1 | 6/2015 | Baxter, III et al. | |
| 2015/0272579 A1* | 10/2015 | Leimbach | A61B 17/07207 227/178.1 |
| 2015/0282809 A1 | 10/2015 | Shelton, IV et al. | |
| 2015/0374364 A1 | 12/2015 | Gettinger et al. | |
| 2016/0100838 A1 | 4/2016 | Beaupre et al. | |
| 2016/0174978 A1* | 6/2016 | Overmyer | A61B 17/07207 227/178.1 |
| 2016/0206310 A1 | 7/2016 | Shelton, IV | |
| 2016/0213438 A1 | 7/2016 | Jogasaki et al. | |
| 2016/0302874 A1 | 10/2016 | Wehrheim et al. | |
| 2018/0168671 A1 | 6/2018 | Overmyer | |
| 2018/0168677 A1 | 6/2018 | Overmyer | |
| 2020/0008828 A1 | 1/2020 | Overmyer | |

FOREIGN PATENT DOCUMENTS

| | | | | |
|---|---|---|---|---|
| EP | 3011911 A1 | 4/2016 | | |
| WO | WO-2014004235 A1 * | 1/2014 | ....... | A61B 17/07207 |
| WO | WO-2014172213 A2 | 10/2014 | | |
| WO | WO-2016057989 A2 | 4/2016 | | |

OTHER PUBLICATIONS

U.S. Appl. No. 15/385,032, filed Dec. 20, 2016, Mark D. Overmyer et al.
International Search Report and Written Opinion for International App. No. PCT/IB2017/057655 dated Jun. 20, 2018 (16 pages).
International Search Report and Written Opinion for International App. No. PCT/IB2017/057657 dated Mar. 27, 2018 (9 pages).
International Search Report and Written Opinion for International App. No. PCT/IB2017/057658 dated Mar. 8, 2018 (15 pages).

* cited by examiner

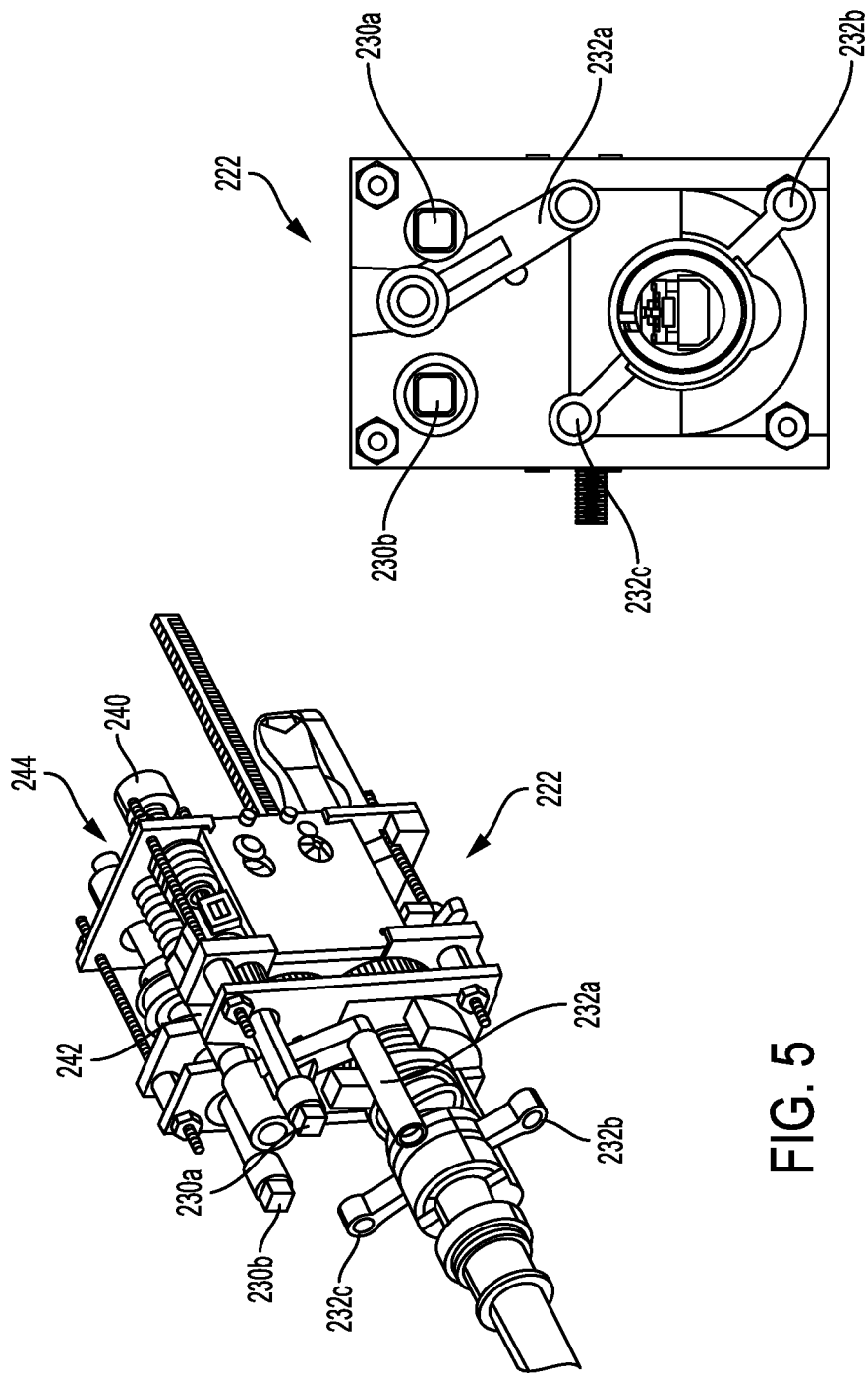

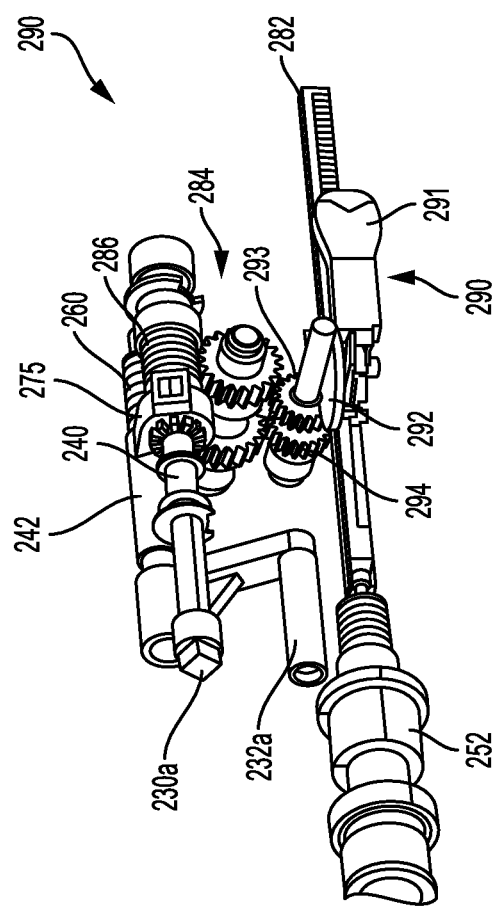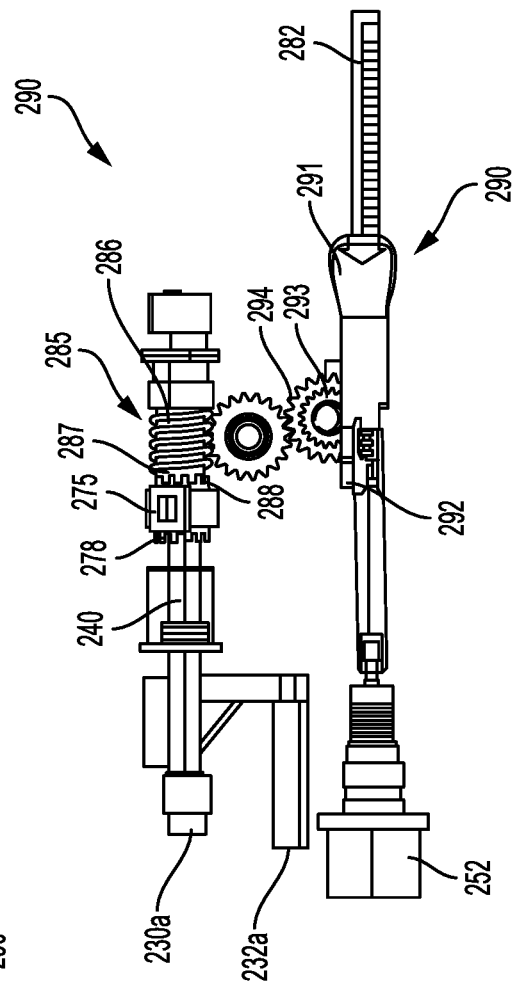
FIG. 8A
FIG. 8B

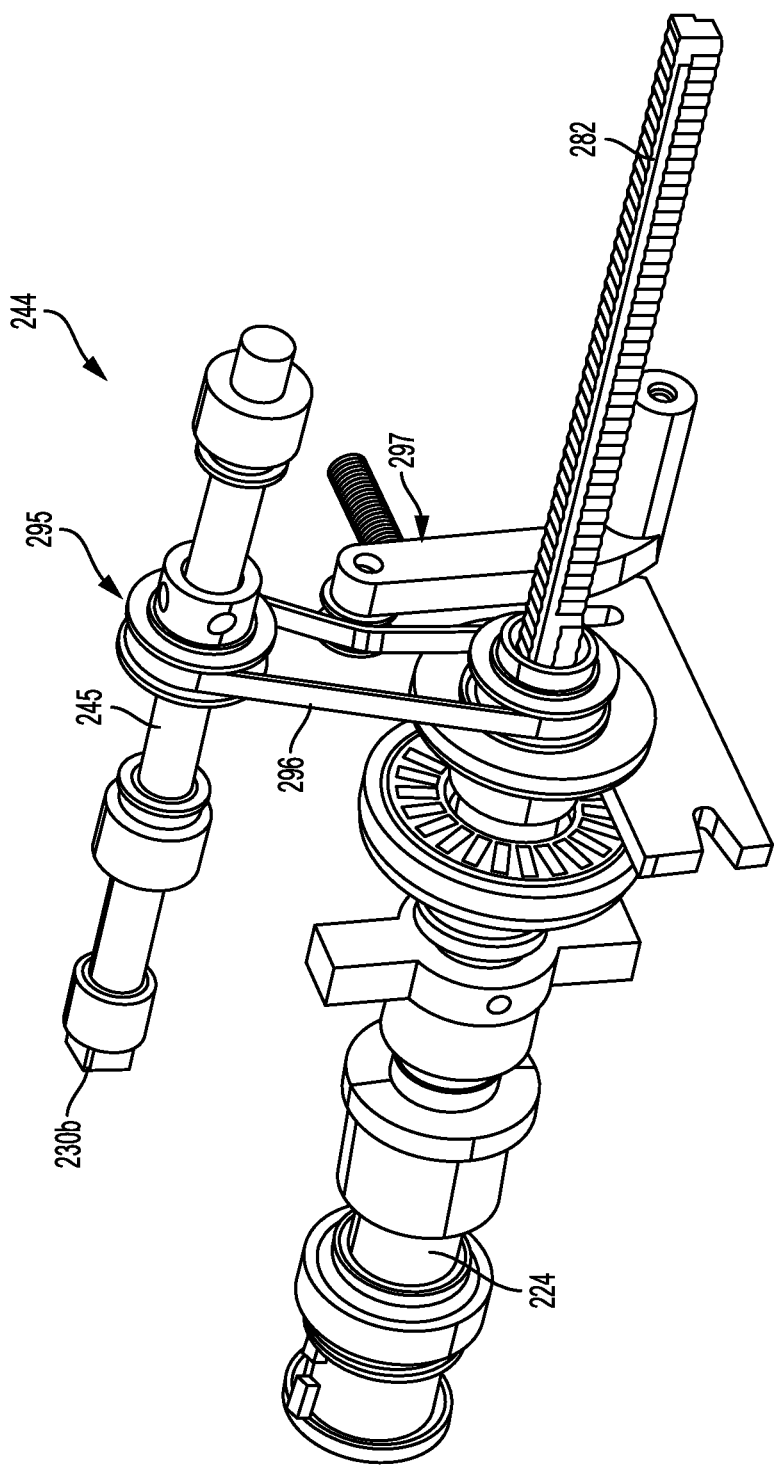

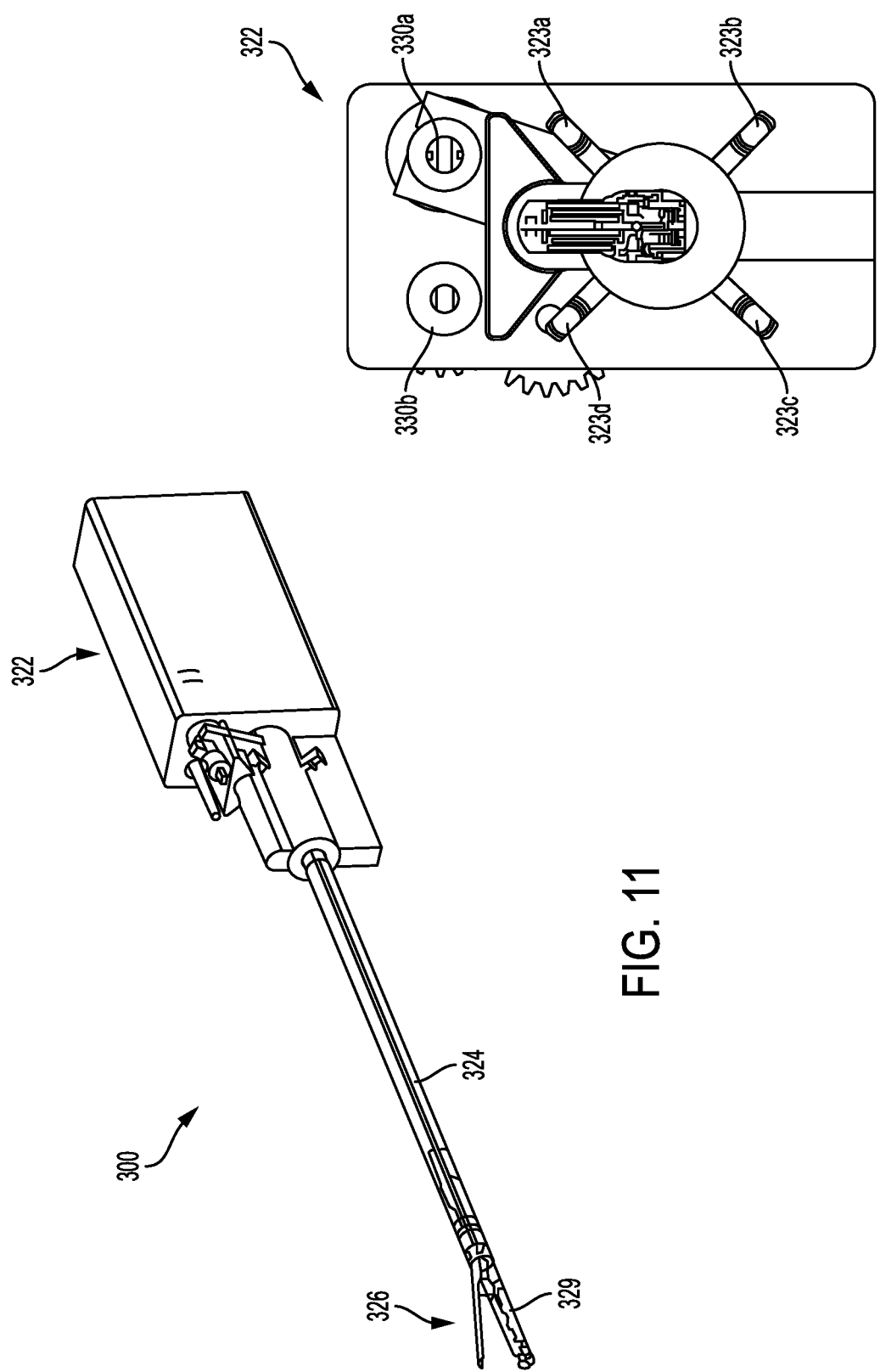

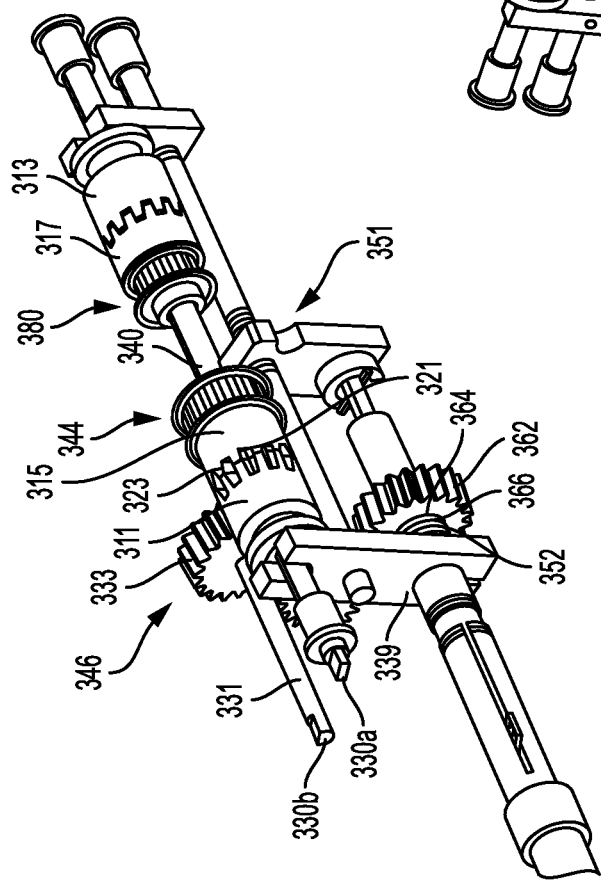
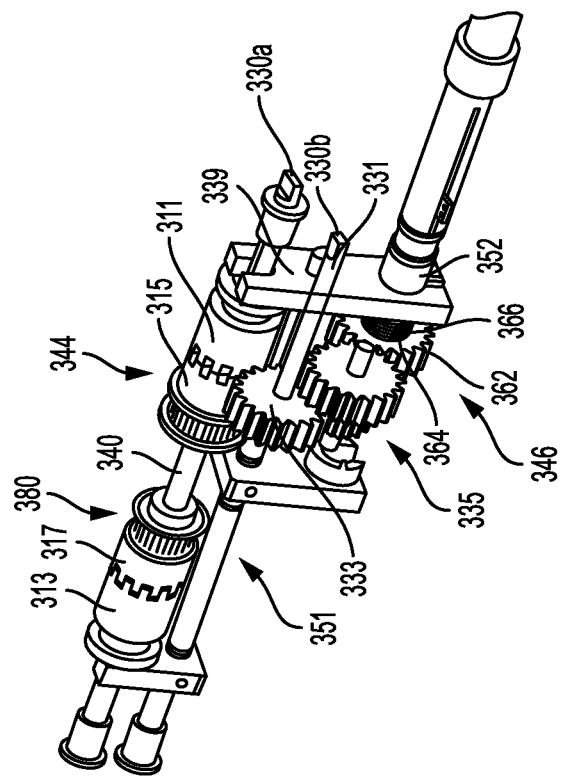
FIG. 13
FIG. 14

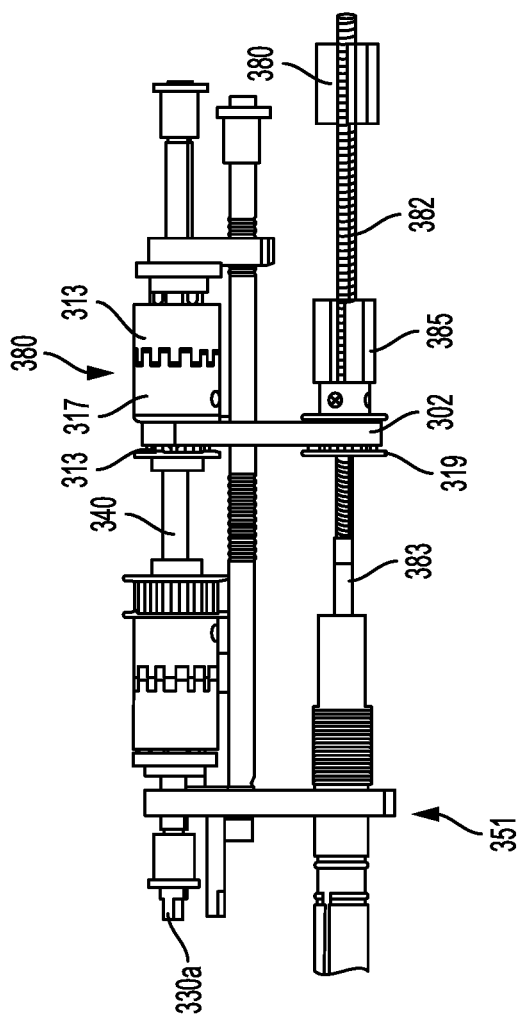
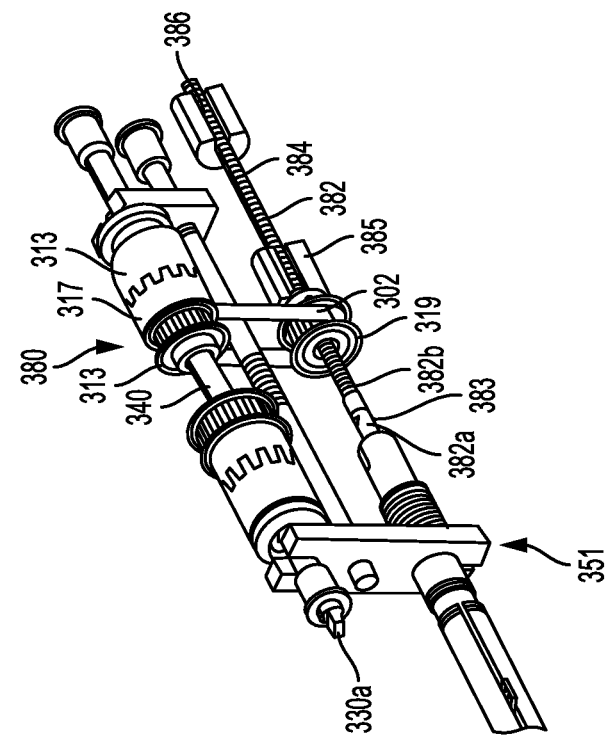
FIG. 19
FIG. 20

ROBOTIC ENDOCUTTER DRIVETRAIN WITH BAILOUT AND MANUAL OPENING

FIELD

Robotic endocutter methods and devices are provided, and in particular an endocutter drivetrain with bailout and manual controls are provided.

BACKGROUND

Minimally invasive surgical (MIS) instruments are often preferred over traditional open surgical devices due to the reduced post-operative recovery time and minimal scarring. Laparoscopic surgery is one type of MIS procedure in which one or more small incisions are formed in the abdomen and a trocar is inserted through the incision to form a pathway that provides access to the abdominal cavity. The trocar is used to introduce various instruments and tools into the abdominal cavity, as well as to provide insufflation to elevate the abdominal wall above the organs. The instruments and tools can be used to engage and/or treat tissue in a number of ways to achieve a diagnostic or therapeutic effect. Endoscopic surgery is another type of MIS procedure in which elongate flexible shafts are introduced into the body through a natural orifice.

Endoscopic surgical instruments are often preferred over traditional open surgical devices since a smaller incision tends to reduce the post-operative recovery time and complications. Consequently, significant development has gone into a range of endoscopic surgical instruments that are suitable for precise placement of a distal end effector at a desired surgical site through a cannula of a trocar. These distal end effectors engage the tissue in a number of ways to achieve a diagnostic or therapeutic effect (e.g., endocutter, grasper, cutter, staplers, clip applier, access device, drug/gene therapy delivery device, and energy device using ultrasound, RF, laser, etc.).

Some endoscopic surgeries require a surgical tool having an end effector positioned at a distal end of an elongate shaft that can perform several functions, such as assist with grasping tissue, cutting tissue, and releasing tissue. Such functions can require various mechanisms to be activated, each of which can require an input from a mechanical driving source (e.g., tool driver). These mechanisms and multiple inputs can add unwanted complexity, size, weight, and cost to endoscopic surgery tools.

SUMMARY

Surgical tools and methods are provided for facilitating bailout and manual opening of a pair of opposed jaws on an endocutter during robotic surgery.

In one embodiment, a surgical tool is provided that includes a housing and an elongate shaft extending distally from the housing. The elongate shaft can include an end effector with opposed jaws on a distal end thereof. A transmission shaft can be disposed within the housing and can be movable between a first position, in which the transmission shaft is configured to be rotated by a rotary input to cause the opposed jaws to move between open and closed positions, and a second position, in which the transmission shaft is configured to be rotated by the rotary input to cause at least one of articulation of the end effector and firing of at least one staple from the end effector.

In some variations one or more of the following features can optionally be included in any feasible combination. The transmission shaft can be configured to move between the first position and the second position in response to linear movement of a linear input. The transmission shaft can couple to a first coupling feature when in the first position to thereby allow rotation of the transmission shaft to actuate a clamping assembly, and actuation of the clamping assembly can cause the opposed jaws to move between the open and closed positions. The transmission shaft can uncouple from the first coupling feature and couples to a second coupling feature when in the second position to thereby allow rotation of the transmission shaft to cause at least one of articulation of the end effector and firing of at least one staple from the end effector.

The surgical tool can further include a shifter coupled to the transmission shaft and configured to be translated by a linear input to effect linear translation of the transmission shaft between the first position and the second position. The clamping assembly can be coupled between the transmission shaft and the end effector and the clamping assembly can include a closure tube configured to translate longitudinally along the elongate shaft to open and close the jaws when the transmission shaft is rotated in the first position. The clamping assembly can include a first gear disposed along the transmission shaft and configured to rotate with the transmission shaft when the transmission shaft is in the first position. The clamping assembly can further include a second gear engaged with the first gear such that the second gear rotates when the first gear rotates. The second gear can include a thru-hole having inner threads that engage outer threads on a proximal end of the closure tube thereby translating the closure tube when the second gear rotates.

The surgical tool can further include a firing assembly coupled between the transmission shaft and the end effector and the firing assembly can include a knife assembly configured to translate longitudinally through the opposed jaws when the transmission shaft is rotated in the second position. The firing assembly can include a worm gear disposed along the transmission shaft and configured to rotate with the transmission shaft when the transmission shaft is in the second position. The firing assembly can further include a pinion gear coupled to the worm gear such that rotation of the worm gear causes the pinion gear to rotate and a rack that is longitudinally translatable relative to the housing to cause corresponding longitudinal translation of the knife assembly through the opposed jaws.

The firing assembly can also include a crossover gear that is coupled between the pinion gear and the rack such that the crossover gear rotates as a result of the pinion gear rotating thereby causing longitudinal translation of the rack. The crossover gear can be movable between an extended position, in which it is engaged with the rack, and a collapsed position, in which it is moved out of engagement with the rack.

The surgical tool can further include a bailout lever configured to move the crossover gear from the extended position to the collapsed position. The bailout lever can include a ratchet feature that engages the rack such that movement of the lever is effective to cause proximal longitudinal translation of the rack.

The surgical tool can further include a roll assembly configured to rotate the end effector about a longitudinal axis of the shaft. The roll assembly can include a pulley configured to be rotated relative to the housing by a third actuation component and the pulley can be coupled to the shaft such that rotation of the pulley effects rotation of the shaft.

In another embodiment, a surgical tool is provided and includes a housing and an elongate shaft extending distally from the housing and having an end effector with opposed jaws on a distal end thereof. The surgical tool can include a transmission shaft having a first part configured to be rotated by a first rotary input to cause at least one of the elongate shaft and the end effector to rotate. The transmission shaft can include a second part configured to be rotated by the first rotary input to fire the end effector. The surgical tool can further include a rack assembly disposed within the housing and longitudinally movable between a first position, in which a first engagement feature of the rack assembly is engaged with the first part of the transmission shaft thereby allowing rotation of the first rotary input to rotate the first part of the transmission shaft, and a second position, in which a second engagement feature of the rack assembly is engaged with the second part of the transmission shaft thereby allowing rotation of the first rotary input to rotate the second part of the transmission shaft. The surgical tool can also include a clamping assembly configured to be rotated by a second rotary input to cause the opposed jaws to move between open and closed positions, wherein the clamping assembly is coupled to the rack assembly and causes the rack assembly to move between the first and second positions when the jaws are moved between open and closed positions.

In some embodiments one or more of the following features can optionally be included in any feasible combination. The clamping assembly can include a closure tube configured to translate longitudinally along the elongate shaft to open and close the jaws. The clamping assembly can also include a closure gear configured to be rotated by the second rotary input, the closure gear including a thru-hole having inner threads that engage outer threads on a proximal end of the closure tube thereby translating the closure tube when the closure gear rotates.

The surgical tool can further include a firing assembly coupled between the transmission shaft and the end effector. The firing assembly can be configured to translate a knife assembly longitudinally through the opposed jaws when the second part of the transmission shaft is rotated and the jaws are closed.

The surgical tool can include a roll assembly coupled between the transmission shaft and the end effector and the roll assembly can be configured to rotate the shaft thereby causing the end effector to rotate. The surgical tool can also include an articulation assembly coupled between the transmission shaft and the end effector. The articulation assembly can include at least one articulation shaft configured to be longitudinally advanced along the elongate shaft by a linear input to cause the end effector to articulate when the jaws are in the closed position.

In another embodiment, a surgical method is provided and can include activating a rotary input to rotate a transmission shaft in a first position where rotation of the transmission shafting causes opposed jaws of an end effector coupled thereto to move between open and closed positions. The method can further include activating a linear input to translate a shifter thereby moving the transmission shaft from the first position to a second position. The method can also include activating the rotary input to rotate the transmission shaft in the second position where rotation of the transmission shaft in the second position can cause articulation of the end effector when the opposed jaws are in the open position, and rotation of the transmission shaft in the second position can advance a knife assembly through the opposed jaws of the end effector when the opposed jaws are in the closed position.

In one embodiment, a surgical method can include rotating a closure gear to translate a closure tube thereby causing opposed jaws of an end effector positioned at a distal end of an elongate shaft of a surgical tool to move between open and closed positions. The method can also include rotating a transmission shaft with a rack assembly coupled to the transmission shaft being in a first position thereby causing the elongate shaft to rotate. Furthermore, the method can include moving the rack assembly into a second position and rotating the transmission shaft with the rack assembly in the second position thereby causing a knife assembly to advance through the opposed jaws of the end effector.

The details of one or more variations of the subject matter described herein are set forth in the accompanying drawings and the description below. Other features and advantages of the subject matter described herein will be apparent from the description and drawings, and from the claims.

BRIEF DESCRIPTION OF THE DRAWINGS

The invention will be more fully understood from the following detailed description taken in conjunction with the accompanying drawings, in which:

FIG. 5 is a side perspective view of a proximal portion of the housing of FIG. 4, with a portion of the outer housing removed;

FIG. 6 is a front view of the housing of FIG. 4 showing two rotary input couplings and three linear input couplings for controlling at least one mechanism of the tool assembly;

FIG. 8A is a side perspective view of a firing assembly of the tool assembly of FIG. 4;

FIG. 8B is a side view of the firing assembly of FIG. 8A;

FIG. 10 is a side perspective view of a roll assembly of the tool assembly of FIG. 4;

FIG. 11 is a side perspective view of another exemplary embodiment of a tool assembly having a housing with at least one rotary input coupling and at least one linear input coupling;

FIG. 12 is a front view of the housing of FIG. 11 showing two rotary input couplings and four linear input couplings for controlling at least one mechanism associated with the tool assembly;

FIG. 13 is a perspective side view of a clamping assembly and a rack assembly that controls activation of a roll assembly or a firing assembly of the tool assembly of FIG. 11;

FIG. 14 is another perspective side view of the clamping assembly and rack assembly of FIG. 13;

FIG. 19 is a side view of the rack assembly of FIG. 13 in the second position and showing the firing assembly that controls translation of an I-beam through the elongate shaft of the tool assembly;

FIG. 20 is a side perspective view of the rack assembly and firing assembly of FIG. 19;

DETAILED DESCRIPTION

Figure 1:
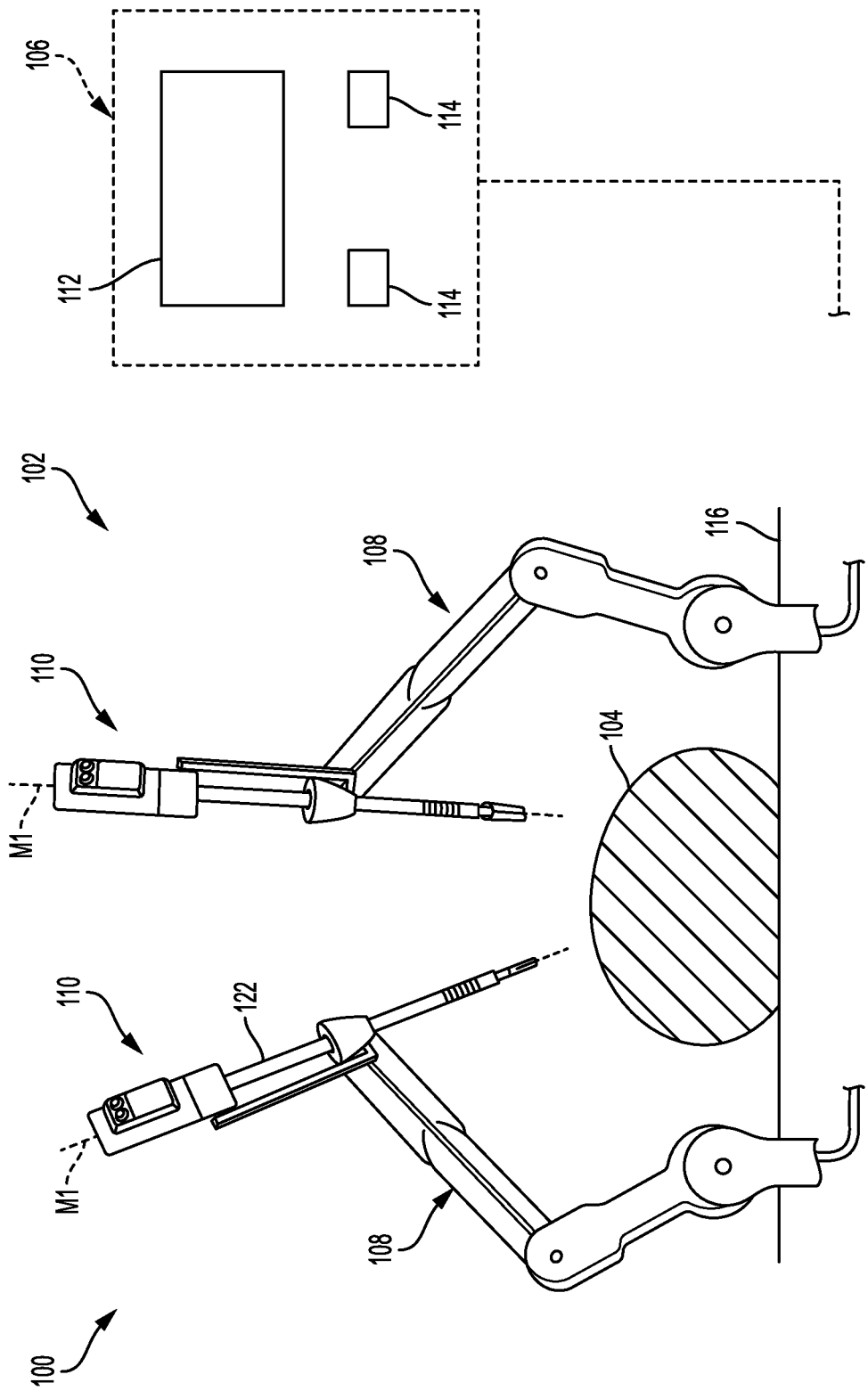
FIG. 1 is a perspective view of one embodiment of a surgical robotic system that includes a patient-side portion and a user-side portion.

Certain exemplary embodiments will now be described to provide an overall understanding of the principles of the structure, function, manufacture, and use of the devices and methods disclosed herein. One or more examples of these embodiments are illustrated in the accompanying drawings. Those skilled in the art will understand that the devices and methods specifically described herein and illustrated in the accompanying drawings are non-limiting exemplary embodiments and that the scope of the present invention is defined solely by the claims. The features illustrated or described in connection with one exemplary embodiment may be combined with the features of other embodiments. Such modifications and variations are intended to be included within the scope of the present invention.

Further, in the present disclosure, like-named components of the embodiments generally have similar features, and thus within a particular embodiment each feature of each like-named component is not necessarily fully elaborated upon. Additionally, to the extent that linear or circular dimensions are used in the description of the disclosed systems, devices, and methods, such dimensions are not intended to limit the types of shapes that can be used in conjunction with such systems, devices, and methods. A person skilled in the art will recognize that an equivalent to such linear and circular dimensions can easily be determined for any geometric shape. Sizes and shapes of the systems and devices, and the components thereof, can depend at least on the anatomy of the subject in which the systems and devices will be used, the size and shape of components with which the systems and devices will be used, and the methods and procedures in which the systems and devices will be used.

In general, various embodiments of a tool assembly that can be used with a robotic surgical system are provided for performing endoscopic surgery. The tool assembly can include more than one mechanical assembly that controls various functions, such as opening and closing jaws of an end effector, advancing a knife assembly or I-beam through the jaws, articulating the end effector relative to an elongate shaft of the tool, and rotating the end effector about a longitudinal axis of the elongate shaft. Such functions can allow the tool assembly to perform a variety of surgical steps and procedures, including grasping and cutting tissue. The tool assemblies can be configured to couple to a tool driver on a surgical robot, thus allowing various motors in the tool drive to control the mechanical assemblies. In an exemplary embodiment, the tool assemblies described herein can include compact drivetrains that minimize the number of inputs (e.g., rotary inputs, linear inputs) that couple to outputs on the surgical robot to perform the tool assembly functions described above. Furthermore, the tool assemblies described herein can include one or more manual or bailout controls that allow a user to manually control one or more of the functions described above. For example, a manual control can be provided for opening and/or closing the jaws and a bailout control can disconnect or disable a mechanism of the tool assembly thereby preventing activation of the mechanism by a mechanical output (rotary or linear). Such manual or bailout control can act as a safety or backup in the event of power failure or other issues. Manual control can also provide the benefit of allowing the tool assembly to be used when disconnected from either a robotic arm or electrical power.

As indicated above, in one embodiment the systems, devices, and methods disclosed herein can be implemented using a robotic surgical system. As will be appreciated by a person skilled in the art, electronic communication between various components of a robotic surgical system can be wired or wireless. A person skilled in the art will also appreciate that all electronic communication in the system can be wired, all electronic communication in the system can be wireless, or some portions of the system can be in wired communication and other portions of the system can be in wireless communication.

FIG. 1 is a perspective view of one embodiment of a surgical robotic system 100 that includes a patient-side portion 102 that is positioned adjacent to a patient 104, and a user-side portion 106 that is located a distance from the patient 104, either in the same room and/or in a remote location. The patient-side portion 102 generally includes one or more robotic arms 108 and one or more tool assemblies 110 that are configured to releasably couple to a robotic arm 108. The user-side portion 106 generally includes a vision system 152 for viewing the patient and/or surgical site, and a control system 112 for controlling the movement of the robotic arms 108 and each tool assembly 110 during a surgical procedure.

The control system 112 can have a variety of configurations and it can be located adjacent to the patient, e.g., in the operating room, remote from the patient, e.g., in a separate control room, or it can be distributed at two or more locations. For example, a dedicated system control console can be located in the operating room, and a separate console can be located in a remote location. The control system 112 can include components that enable a user to view a surgical site of a patient being operated on by the patient-side portion 102 and/or to control one or more parts of the patient-side portion 102 (e.g., to perform a surgical procedure at the surgical site). In some embodiments, the control system 112 can also include one or more manually-operated user input devices 114, such as a joystick, exoskeletal glove, a powered and gravity-compensated manipulator, or the like. These user input devices can control teleoperated motors which, in turn, control the movement of the surgical system, including the robotic arms 108 and tool assemblies 110.

The patient-side portion can also have a variety of configurations. As depicted in FIG. 1, the patient-side portion 102 can couple to an operating table 116. However, in some embodiments, the patient-side portion 102 can be mounted to a wall, to the ceiling, to the floor, or to other operating room equipment. Further, while the patient-side portion 102 is shown as including two robotic arms 108, more or fewer robotic arms 108 may be included. Furthermore, the patient-side portion 102 can include separate robotic arms 108 mounted in various positions, such as relative to the surgical table 116 (as shown in FIG. 1). Alternatively, the patient-side portion 102 can include a single assembly that includes one or more robotic arms 108 extending therefrom.

Figure 2:
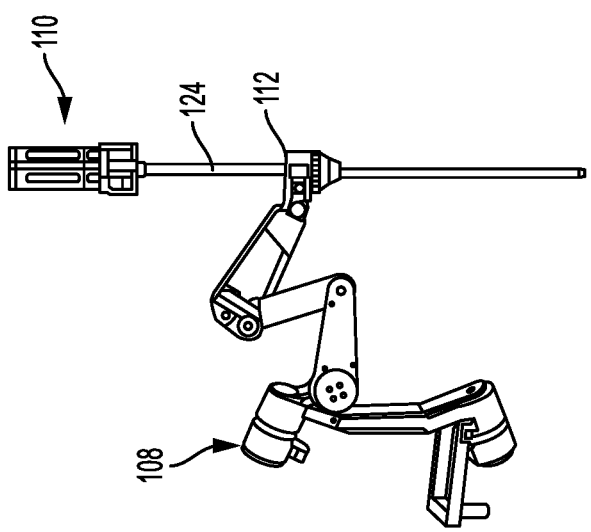
FIG. 2 is a perspective view of a robotic arm and tool assembly of FIG. 1.

FIG. 2 illustrates the robotic arm 108 and tool assembly 110 releasably coupled to the robotic arm 108 in more detail. The robotic arm 108 can support and move the associated tool assembly 110 along one or more mechanical degrees of freedom (e.g., all six Cartesian degrees of freedom, five or fewer Cartesian degrees of freedom, etc.).

The robotic arm 108 can include a tool driver 112 at a distal end of the robotic arm 108, which can assist with controlling features associated with the tool assembly 110. While not shown, the tool driver 112 can include one or more motors with shafts that either rotate or translate, and that couple to the tool assembly to effect motion of various components of the tool assembly. The robotic arm 108 can also include an entry guide (e.g., a cannula mount or cannula) that can be a part of or removably coupled to the robotic arm 108, as shown in FIG. 2. A shaft of the tool assembly 110 can be inserted through the driver 112 and the cannula for insertion into a patient. A person skilled in the art will appreciate that the configuration of the robotic arm can vary, and that the tool assemblies disclosed herein can be used with any robotic arm.

In order to provide a sterile operation area while using the surgical system, a barrier (not shown) can be placed between the actuating portion of the surgical system (e.g., the robotic arm 108) and the surgical instruments (e.g., the tool assembly 110). A sterile component, such as an instrument sterile adapter (ISA) (not shown), can also be placed at the connecting interface between the tool assembly 110 and the robotic arm 108. The placement of an ISA between the tool assembly 110 and the robotic arm 108 can ensure a sterile coupling point for the tool assembly 110 and the robotic arm 108. This permits removal of tool assemblies 110 from the robotic arm 108 to exchange with other tool assemblies 110 during the course of a surgery without compromising the sterile surgical field.

Figure 3:
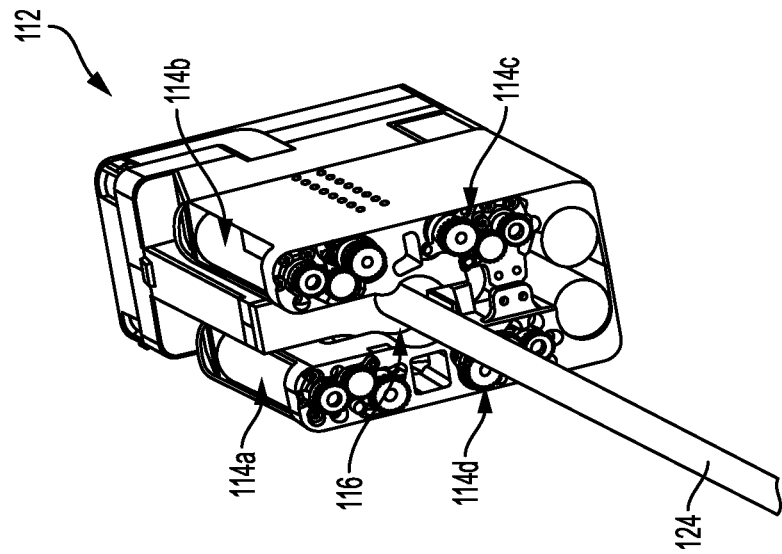
FIG. 3 is a perspective view of a tool driver of the robotic arm of FIG. 2.

FIG. 3 illustrates the tool driver 112 in more detail. As shown, the tool driver 112 can include one or more motors, e.g., four motors 114a-114d are shown, that control a variety of movements and actions associated with the tool assembly 110, as will be described in greater detail below. For example, each motor 114a-114d can couple to and/or interact with a coupling or activation feature (e.g., gear) associated with the tool assembly 110 for controlling one or more actions and movements that can be performed by the tool assembly 110, such as for assisting with performing a surgical operation. The motors 114a-114d can be accessible on an upper surface of the tool driver 112, and thus the tool assembly can be configured to mount on top of the tool driver 112 to couple thereto. The tool driver 112 can also include a shaft-receiving channel 116 formed in a sidewall thereof for receiving the shaft of the tool assembly 110. In other embodiments, the shaft can extend through on opening in the tool driver 112, or the two components can mate in various other configurations.

The tool assembly 110 can include a housing 122 coupled to a proximal end of a shaft 124 and an end effector coupled to a distal end of the shaft 124. The end effector can include a pair of jaws, such as a second jaw that pivots relative to a first jaw. The second jaw can pivot between an open position where the pair of jaws are configured to receive tissue therebetween and a closed position where the pair of jaws are configured to engage tissue therebetween. In one embodiment, the first jaw can be configured to house a staple cartridge containing multiple staples, and the second jaw can be an anvil for forming the staples. In some embodiments the end effector can include a knife assembly, such as an I-beam, that can be advanced between the jaws, such as to fire staples and cut tissue captured between the jaws. The housing 122 can include coupling features that assist with releasably coupling the housing 122 to the tool driver 112 of the robotic arm 108. The housing 122 can include gears and/or actuators that can be actuated by the one or more motors 114a-114d in the driver 112, as will be described in greater detail below. The gears and/or actuators in the housing 122 can control the operation of various features associated with the end effector (e.g., clamping, firing, rotation, articulation, etc.), as well as control the movement of the shaft 124 (e.g., rotation of the shaft).

The shaft 124 can include actuators and connectors that extend along the shaft and assist with controlling the actuation and/or movement of the end effector (e.g., opening and closing of the jaws) and/or shaft 124. The shaft 124 can also include one or more joints or wrists 128 that allow a part of the shaft 124 or the end effector to articulate relative to the longitudinal axis of the shaft 124. This can allow for fine movements and various angulation of the end effector relative to the longitudinal axis of the shaft 124. The end effector can include any of a variety of surgical tools, such as a stapler, a clip applier, forceps, a needle driver, a cautery device, a cutting tool, a pair of jaws, an imaging device (e.g., an endoscope or ultrasound probe), or a combined device that includes a combination of two or more various tools.

In one exemplary embodiment, the housing 122 can have at least one rotary input coupling and at least one linear input coupling for allowing either a rotary output or a linear output from the tool driver 112 to activate at least one mechanism of the tool assembly. For example, the at least one mechanism of the tool assembly can include one or more of a clamping assembly, a firing assembly, an articulation assembly, and a rotation/roll assembly. The clamping assembly can be configured to cause opening and closing of the opposed jaws of the end effector. The firing assembly can be configured to cause a I-beam to translate through the end effector for firing staples and cutting tissue. In other embodiments, the firing assembly can cause energy delivery, or other actions to occur depending on the configuration of the end effector. The articulation assembly can be configured to cause the end effector to articulate relative to the elongate shaft. The roll assembly can be configured to cause the elongate shaft and end effector to rotate about a longitudinal axis of the elongate shaft. In some embodiments, a single rotary input and/or linear input can control more than one of these mechanisms. As such, the tool assemblies disclosed herein include multiple functionalities while minimizing the need for mechanical outputs thereby resulting in smaller, more efficient and effective tool assemblies. Furthermore, some of the embodiments can include one or more mechanisms that can be manually controlled and/or disconnected from the tool driver, which can provide a safety mechanism and/or ability to control the tool assembly while disconnected from the robotic arm.

Figure 4:
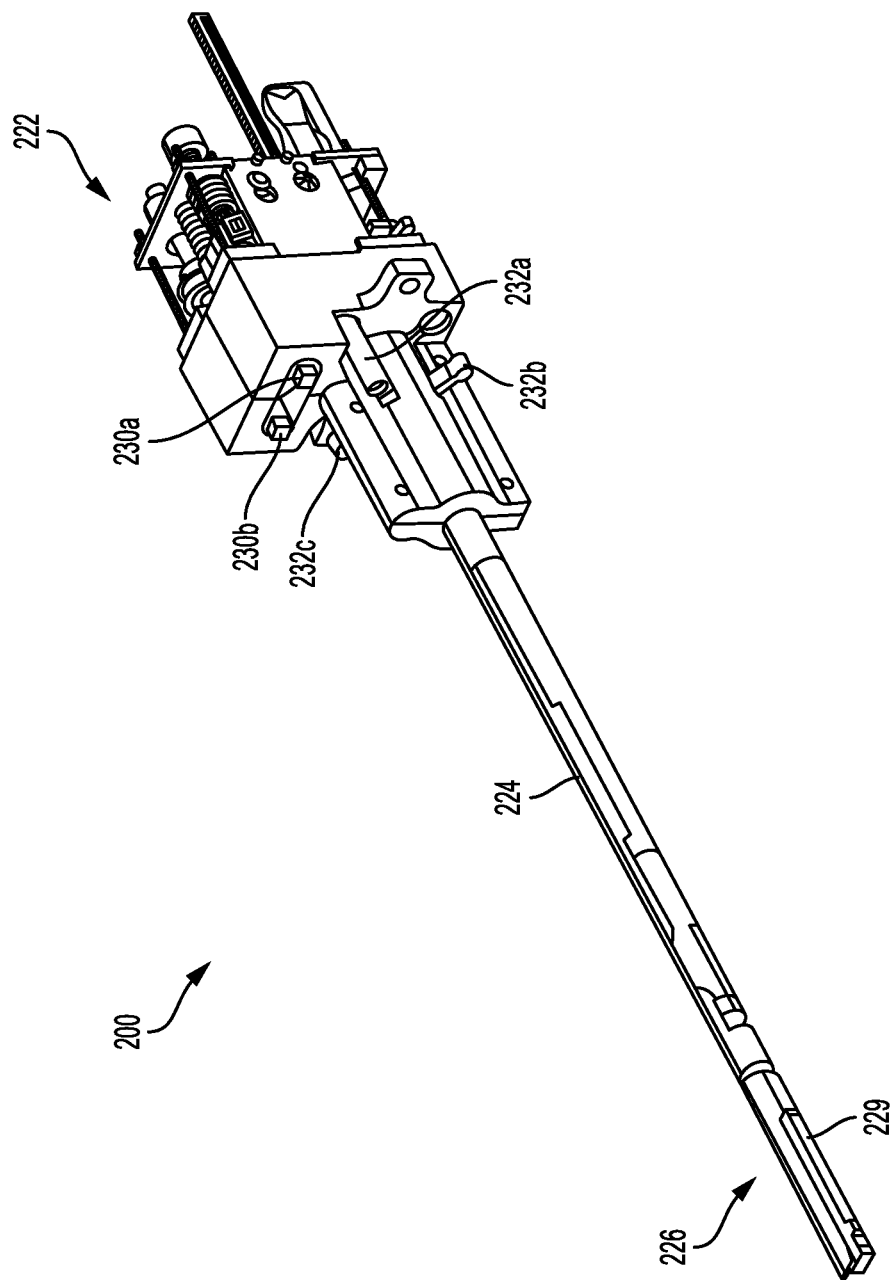
FIG. 4 is a side perspective view of one exemplary embodiment of a tool assembly having a housing with at least one rotary input coupling and at least one linear input coupling.

FIG. 4 illustrates an exemplary embodiment of a tool assembly 200 showing a housing 222 (with part of the outer housing hidden) having a first and second rotary input coupling 230a, 230b and first, second, and third 232a, 232b, 232c linear input couplings. The rotary input couplings 230a, 230b are each configured to couple to a rotary output, such as a rotary actuation motor 114 of the tool driver 112, and the linear input couplings 232a, 232b, 232c are each configured to couple to a linear output, such as a linear actuation motor 114 of the tool driver 112. The interface or coupling between a rotary input coupling and a rotary output or between a linear input coupling and a linear output can include any number of a variety of couplings, all of which are within the scope of this disclosure.

As shown in FIG. 4, the tool assembly 200 can include an elongate shaft 224 extends from the housing 222 and that includes an end effector 226 positioned at a distal end of the elongate shaft 224. The end effector 226 can include a pair of opposed jaws 229 that can pivot between open and configurations, as will be described in greater detail below. The jaws 229 can be configured to grasp tissue therebetween, such as for advancing a I-beam through the end effector 226 to fire staples and cut the stapled tissue.

FIG. 4, as well as FIGS. 5-6, illustrate first and second rotary input couplings 230a, 230b that are configured to couple to first and second rotary outputs on a tool driver of a surgical robot, respectively. The housing 222 includes a transmission shaft 240 having a first end that includes the first rotary input coupling 230a configured to couple to the first rotary output on a tool driver. As such, when the first rotary input coupling 230a is forced to rotate by the first rotary output of the tool driver, the transmission shaft 240 rotates about its longitudinal axis. As will be discussed in greater detail below, the transmission shaft 240 can be configured to assist with controlling and/or activating at least one mechanism of the tool assembly, such as a clamping assembly, an articulation assembly, and/or a firing assembly.

As further shown in FIGS. 4-6, the housing 222 can further include a first linear input coupling 232a that is configured to couple to a first linear output of a tool driver of a surgical robot. The housing 222 can also include a biasing shaft 242, with the first linear input coupling 232a positioned at a distal end of the biasing shaft 242. The biasing shaft can also be coupled to the transmission shaft 240, such as via an extension that extends and couples the biasing shaft to the transmission shaft 240. As such, activation of the first linear input by an output on a tool driver can cause translation of the biasing shaft 242 thereby translating the transmission shaft 240.

The second rotary input coupling 230b can be mechanically coupled to a roll assembly 244 such that when the second rotary input coupling 230b is forced to rotate by the second rotary output on a tool driver, the roll assembly 244 is activated thereby causing the elongate shaft 224 and end effector 226 to rotate about the longitudinal axis of the elongate shaft 224.

The housing 222 can further include second and third linear input couplings 232b, 232c that are each configured to couple to second and third linear outputs on a tool driver of a surgical robot, respectively. For example, the second and third linear input couplings 232b, 232c can be a part of a clamping assembly 246 that controls the opening and closing of the opposed jaws 229, as will be described in greater detail below.

Figure 7:
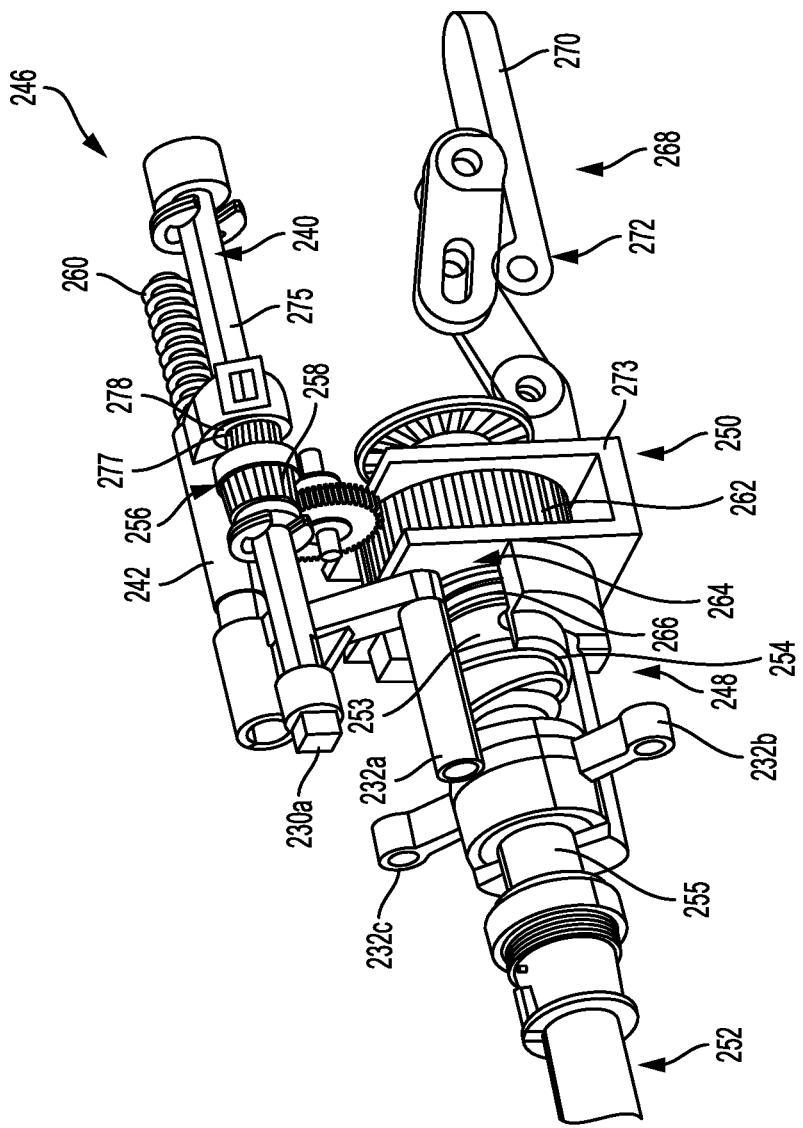
FIG. 7 is a side perspective view of a clamping assembly of the tool assembly of FIG. 4.

FIG. 7 illustrates the clamping assembly 246 of the tool assembly 200 that can be controlled by at least one of a rotary or linear output of a tool driver on a surgical robot, and a manual input on the tool assembly 200 for opening and closing the opposed jaws 229 of the end effector 226. The clamping assembly can include a closure tube 252 that extends between the jaws 229 and at least one of the rotary, linear, and manual inputs. Movement of the closure tube 252, such as linear translation in a proximal and/or distal direction, can cause the jaws to open and/or close. For example, when the closure tube 252 is in the proximal position, the opposed jaws 229 can be forced into an open configuration. When the closure tube 252 is in the distal position, the opposed jaws 229 can be forced into a closed configuration. Furthermore, in some embodiments, the closure tube 252 can include a proximal part 253 and a distal part 255 that are slidably engaged with each other and either individually or together assist with controlling the opening and/or closing of the jaws, as will be described in greater detail below.

The transmission shaft 240 can include a longitudinal or rotational axis, and it can be forced to rotate about this axis via the first rotary input coupling 230a once the first rotary input has been activated. As shown in FIG. 7, the transmission shaft 240 can further include a movable part 275 that is configured to translate along the transmission shaft 240 and is forced to rotate about the longitudinal axis when the transmission shaft 240 rotates. The movable part 275 can be coupled to the biasing shaft 242 and configured to translate along the longitudinal axis of the transmission shaft thereby engaging and/or activating the clamping assembly or firing assembly, as will be described in greater detail below.

The transmission shaft can include a first part 256 that is slidably engaged with the longitudinal axis of the transmission shaft such that it does not rotate unless engaged with the movable part 275. When engaged, the movable part 275 can force the first part 256 to rotate. The first part 256 can include a first coupling feature 277 that is configured to engage a distal coupling feature 278 of the moveable part 275 thereby allowing rotational torque to be transferred from the movable part to the first part 256.

As shown in FIG. 7, the clamping assembly 246 can further include a quick-close sub-assembly 248 and a slow close sub-assembly 250 that each provide different jaw closure speeds and jaw closing forces. For example, the slow-close sub assembly 248 can include the transmission shaft 240 positioned in a first transmission position, as shown in FIG. 7. In the first transmission position, the movable part 275 of the transmission shaft 240 can be engaged with the first part 256 having a first closure gear 258. The first closure gear 258 can be slidably disposed about the longitudinal axis of the transmission shaft 240 and rotationally fixed relative to the first part 256 such that rotation of the first part 256 causes the first closure gear 258 to rotate. As such, the engagement between the first closure gear 258 and the transmission shaft can allow rotational torque from the rotating transmission shaft (e.g., via first rotary input) to cause the first closure gear 258 to rotate.

The first closure gear 258 can be engaged with a second closure gear 262 that is coupled to the proximal part 253 of the closure tube 252, such as via a threaded engagement between inner threads along a thru-hole 264 of the second closure gear and outer threads 266 along the proximal part 253 of the closure tube 252. The threaded engagement between the second closure gear 262 and the proximal part 253 can allow rotation of the second closure gear 262 to cause translation of the proximal part 253 (and not the distal part 255) of the closure tube 252. For example, the proximal part 253 can be prevented from rotating thereby forcing the proximal part 253 to translate when the second closure gear 262 rotates. In some implementations, the second closure gear 262 can translate the proximal part 253 of the closure tube 252 a distance in the distal direction such that the proximal part 253 abuts the distal part 255 and pushes the distal part 255 distally along with the proximal part 253. In this way, both the proximal part 253 and the distal part 255 of the closure tube 252 force the jaws to close.

The quick close sub-assembly 248 can include the second and third linear input couplings 232a, 232b coupled to the distal part 255 of the closure tube 252. Activation of a second and third linear output (e.g., from the tool driver 112) can result in linear translation of the second and third linear input couplings 232a, 232b in the proximal direction, thereby moving the proximal part 253 of the closure tube 252 from a distal position to a proximal position and opening the jaws.

In some implementations, a biasing member 254 (e.g., spring) positioned at a proximal end of the distal part 253 of the closure tube 252 can force the distal part 253 of the closure tube 252 in the distal direction (thereby closing the opposed jaws), such as when the second and third linear outputs are not activated. As such, in the quick-close sub-assembly, the biasing member 254 provides the force to move the distal part 253 of the closure tube 252 into the distal position to close the jaws. Furthermore, the biasing member 254 can assist with controlling the rate of closure of the jaws, which can be relatively fast compared to the jaw closure by the slow-close sub-assembly 250 (e.g., rotation of the second closure gear 262). However, although the quick-close sub-assembly 248 can provide faster closing of the jaws, the jaw closure force applied by the quick-close sub-assembly 248 can be less than the jaw closure force provided by the slow-close sub-assembly 250. As such, the quick-close sub-assembly 248 can be beneficial when fast closing of the jaws is needed and the slow-close sub-assembly 250 can be beneficial when a greater clamping force is needed to close the jaws 229.

In some embodiments, the clamping assembly 246 can include a manual sub-assembly 268 that allows manual control by a user to control the opening and closing of the jaws. As shown in FIG. 7, the manual sub-assembly 268 can include a closure lever 270 that is accessible to a user (e.g., via an opening in the housing) to pivot from a closed lever position where the jaws are in the closed position to an open lever position where the jaws are in an open position. The manual sub-assembly 268 can include, for example, a series of jointed links 272 that extend between the closure lever 270 and a bracket 273 coupled to the second closure gear 262. This configuration can allow pivoting of the lever 270 from the closed lever position to the open lever position to proximally translate the bracket 273 and cause the second closure gear 262 to translate proximally (along with the closure tube 252) thereby causing the jaws to open. Pivoting of the closure lever 270 back to the closed lever position can translate the bracket 273 distally thereby distally translating the second closure gear 262 and closing the jaws.

As shown in FIG. 7, the transmission shaft 240 can be biased in the first transmission position by a transmission biasing member (e.g., spring) 260. For example, the transmission biasing member 260 can act against the biasing shaft 242 coupled to the first linear input coupling 230a and the transmission shaft 240. As such, activation of the first linear output on the tool driver can cause proximal translation of the first linear input coupling 230a and the biasing shaft 242, thereby compressing the transmission biasing member 260 and moving the transmission shaft 240 from the first transmission position to the second transmission position, such as for activating the firing assembly, as will be discussed in greater detail below. Deactivation of the first linear output can cause the transmission biasing member 260 to reform or decompress thereby moving the transmission shaft back to the first transmission position, such as for activating the clamping assembly 246.

FIGS. 8A and 8B illustrate a firing assembly 280 of the tool assembly 200 that can be controlled by at least one of a rotary input, a linear input, and a manual input for controlling either the translation of an I-beam through the end effector 226 or articulation of the end effector 226. For example, activation of the firing mechanism 280 can cause translation of the I-beam when the jaws 229 are closed and activation of the firing mechanism 280 can cause articulation of the end effector 226 when the jaws are open. An assembly for shifting between articulation mode and firing mode is disclosed in more detail in U.S. Publication No. 2015/0272579 entitled "Modular Powered Surgical Instrument with Detachable Shaft Assemblies," which is hereby incorporated by reference herein in its entirety. The firing assembly can include a rack 282 that is operably coupled to the I-beam such that translational movement of the rack 282 causes translational movement of the I-beam through the jaws 229, such as for firing staples and cutting tissue captured between the jaws 229. For example, distal movement of the rack 282 can cause the I-beam to advance distally through the jaws and proximal movement of the rack 282 can cause the I-beam to retract proximally through the jaws.

In some implementations, as described in more detail in U.S. Publication No. 2015/0272579, a distal end of the rack 282 can be coupled at to a firing rod. When the rack 282 is forced to translate in the distal direction, for example, the firing rod can also be forced to translate in the distal direction. Similarly, if the rack 282 is forced to translate in the proximal direction, the firing rod can be forced to translate in the proximal direction. The firing rod can be coupled to a shifter that is configured to shift the firing rod between a firing configuration (e.g., when the jaws 229 are in a closed configuration) and an articulation configuration (e.g., when the jaws are in an open configuration). The shifter can be coupled to and/or controlled by the closure tube 252 such that movement of the closure tube 252 to either open or close the jaws 229 causes the shifter to move thereby transitioning the firing rod between the firing and articulation configurations. When the jaws 229 are open and the firing rod is in the articulation configuration, the firing rod can be engaged with the articulation shaft such that translation of the firing rod causes movement of an articulation shaft, thereby causing the end effector 226 to articulate. Furthermore, when the jaws 229 are open, the firing rod can be disconnected from the I-beam. When the jaws 229 are closed and the firing rod is in the firing configuration, the firing rod can be connected to the I-beam and disconnected from the articulation shaft. As such, translation of the firing rod can cause movement of the I-beam through the jaws 229. For example, distal translation of the firing rod can distally advance the I-beam to fire staples and cut tissue positioned between the jaws 229.

The rack 282 can be advanced either mechanically, such as when coupled to a robotic arm, or manually by a user. For example, the firing assembly 280 can include a firing gear train 284 that, when caused to rotate, causes the rack 282 to translate. As shown in FIGS. 8A and 8B, the rack 282 can be coupled to the transmission shaft 240 via the gear train 284 such that rotation of the transmission shaft 240 causes rotation of the gear train 284 and translation of the rack 282.

In some implementations, the transmission shaft 240 can include a second part 285 that includes a worm gear 286 and a second coupling feature 287. Similar to the first part 256, the second part of the transmission shaft 240 can be slidably disposed along the longitudinal axis of the transmission shaft 240 such that the second part 285 (including the worm gear 286) does not rotate when the transmission shaft 240 rotates unless the second part 285 is engaged and rotationally locked to the movable part 275. For example, when the transmission shaft 240 is in the second position, a proximal coupling feature 288 of the movable part 275 can be engaged with the second coupling feature 287 of the second part 285 such that rotation of the transmission shaft (e.g., from activation of the first rotary input) causes rotation of the second part 285. Rotation of the second part 285 can cause the worm gear 286 and the firing gear train 285 to rotate thereby translating the rack 282. As such, when the transmission shaft 240 is in the second position, activation of the first rotary input causes the second part 285 of the transmission shaft to rotate thereby causing the I-beam to translate through the jaws.

The firing assembly 280 can include a bailout sub-assembly 290 that includes a lever 291 that can pivot relative to the rack 282. The lever 291 can be operatively coupled to the rack 282 such that movement of the lever 291 (e.g., pivoting from a first pivot position to a second pivot position) can cause the rack 282 to translate and the I-beam to move. For example, the lever 291 can include engagement teeth that engage rack features along a length of the rack 282 such that pivoting the lever 291 from the first pivot position to the second pivot position causes the engagement teeth to apply a force against the rack 282 thereby forcing the rack to translate a distance in the distal direction. This can cause the I-beam to also advance the same or similar distance through the jaws. For example, the lever 291 can be configured similar to a ratchet such that movement (e.g., pivoting) of the lever 291 relative to the rack 282 can cause incremental movement of the rack 282 thereby incrementally moving the I-beam through the jaws. This configuration can be useful, for example, when the tool assembly 200 is being manually controlled, such as before or after the tool assembly is coupled to a robotic arm.

As shown in FIG. 8A, the bailout sub-assembly 290 can include a decoupler 292 that decouples the gear train 284 from the rack 282 when the lever 291 is initially moved or pivoted. The decoupler 292 can be positioned between the lever 291 and a crossover gear 293 of the gear train 284 such that when the lever 291 is initially pivoted, the lever 291 causes the decoupler 292 to move (e.g., pivot) thereby causing the crossover gear 293 to translate from an engaged position to a disengaged position. In the engaged position, the crossover gear 293 is engaged with the rack 282 and a part of the gear train 284 such that rotation of the first rotary input causes the crossover gear 293 to rotate, which causes the rack 282 to translate. In the disengaged position, the crossover gear 293 is disengaged from the rack 282 such that activation of the first rotary input and rotation of the crossover gear 293 does not cause the rack 282 to translate. However, the lever 291 of the bailout sub-assembly 290 still allows for manual translation of the rack 282. This can be useful when a user wants to manually adjust or control positioning of the I-beam, such as when the tool assembly is decoupled from the robotic arm. Manual control of the tool assembly can also be useful when there is loss of power or the tool assembly is experiencing technical difficulties (e.g., the I-beam jammed during firing).

Various tool assemblies can include one or more features that allow for manual control of one or more mechanisms. Manual control of some mechanisms can allow the tool assembly to be used at least before or after the tool assembly is coupled to a robotic arm. For example, manual control can be useful when there are mechanical or power issues with either the robotic arm or tool assembly.

Figure 9A:
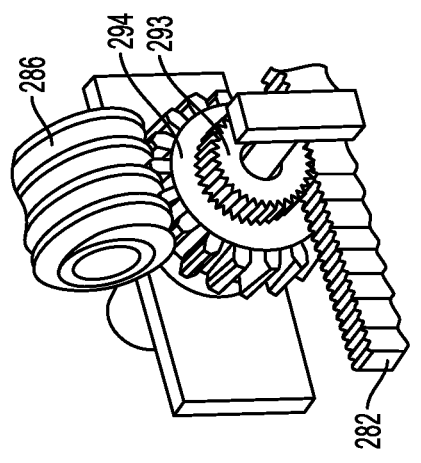
FIG. 9A is a side perspective view of a crossover gear of a bailout sub-assembly of the firing assembly of FIG. 8A shown in an engaged configuration.
Figure 9B:
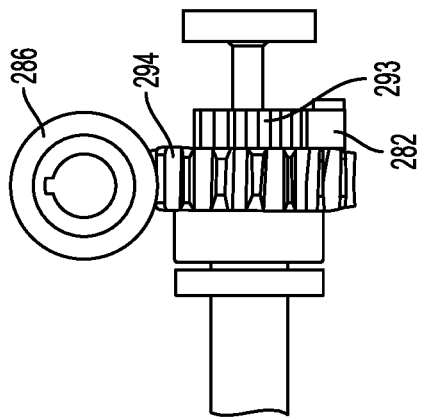
FIG. 9B is a side view of the bailout sub-assembly of FIG. 9A shown in the engaged configuration.
Figure 9C:
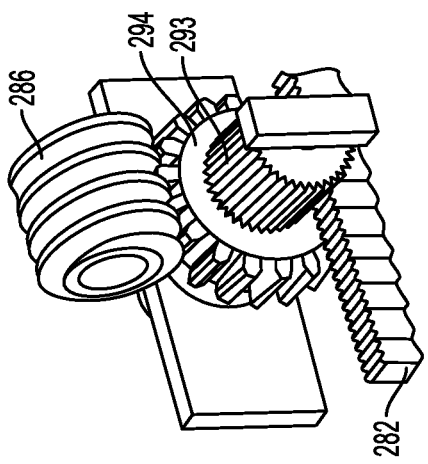
FIG. 9C is a side perspective view of the crossover gear of the bailout sub-assembly of FIG. 9A shown in a manual configuration.
Figure 9D:
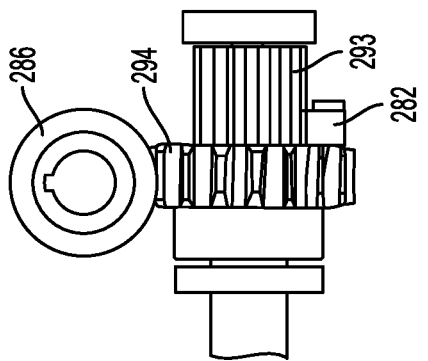
FIG. 9D is a side view of the bailout sub-assembly of FIG. 9C shown in a manual configuration.
Figure 9E:
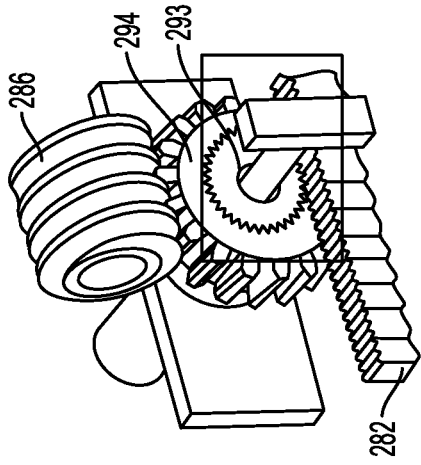
FIG. 9E is a side perspective view of the crossover gear of the bailout sub-assembly of FIG. 9A shown in a disengaged configuration.
Figure 9F:
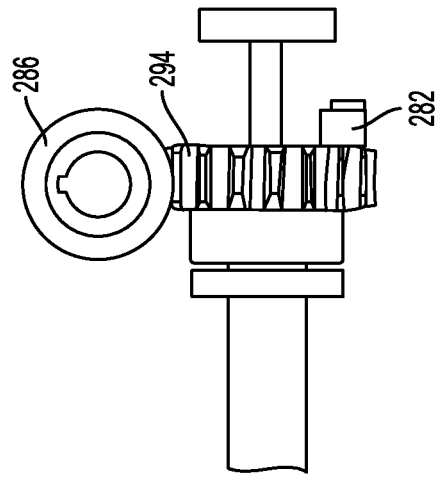
FIG. 9F is a side view of the bailout sub-assembly of FIG. 9E shown in the disengaged configuration.

As shown in FIGS. 9A-9F, some embodiments of the bailout sub-assembly 290 can include a crossover gear 293 configured to be positioned in a fully engaged configuration (see FIGS. 9A-9B), a manual configuration (see FIG. 9C-9D), or a bailout configuration (see FIG. 9E-9F). In the fully engaged configuration, as shown in FIGS. 9A-9B, the crossover gear 293 is positioned to engage the rack 282 for translating the rack 282 when the crossover gear 293 is caused to rotate (e.g., by the gear train 284 and first rotary input). As shown in FIGS. 9A-9B, the worm gear 286 is engaged with a pinion gear 294 having a through hole with splines that are configured to engage outer features along the crossover gear 293 of which the pinion gear 294 is slidably coupled to. For example, the through hole of the pinion gear 294 includes splines that are sized and shaped to allow the crossover gear 293 to linearly translate along a rotational axis shared by the crossover gear and the pinion gear. Such splines of the pinion gear 294 also provide torque to the outer features of the crossover gear 293 thereby causing the crossover gear 293 to rotate when the pinion gear 294 is forced to rotate by the worm gear 286.

As shown in FIGS. 9C-9D, the crossover gear 293 can be placed in the manual configuration by slidably translating the crossover gear 293 relative to the pinion gear 294 such that the crossover gear 293 is engaged with the rack 282 but is no longer slidably engaged with the pinion gear 294. For example, access through the housing 222 of the tool assembly can allow a user to manually rotate the crossover gear 293 thereby translating the rack 282 to advance or retract the I-beam. In some embodiments, translation of the rack can also assist with opening or closing the jaws.

As shown in FIGS. 9E-9F the crossover gear 293 can be slidably translated relative to the pinion gear 294 such that the crossover gear 293 is engaged with the pinion gear 294 but is no longer engaged with the rack 282. In this configuration, rotation of the pinion gear 294 (e.g., as a result of activation of the first rotary input) does not cause translation of the rack 282. This can provide a safety mechanism to ensure that either the jaws do not pivot or the I-beam does not translate when it is dangerous to do so.

The crossover gear 293 can move between the engaged configuration, the manual configuration, and the bailout configuration manually or by activating a mechanism (e.g., bailout sub-assembly). As discussed above, a pivoting lever 291 of the bailout sub-assembly 290 can cause a decoupler 292 to push the crossover gear 293 into the bailout configuration. A user can also manually change configurations of the crossover gear, such as by sliding the crossover gear from the engaged configuration to the manual configuration. In the bailout configuration, the rack cannot be translated mechanically, however it can be translated manually, e.g., by the pivoting lever described above.

FIG. 10 illustrates a perspective view of the roll assembly 244 of the tool assembly 200 that can be controlled by a second rotary input for controlling rotation of the end effector 226 about a longitudinal axis of the elongate shaft 224 of the tool assembly 200. As shown in FIG. 10, the roll assembly 244 can include a roll shaft 245 coupled to the second rotary input coupling 230b that is configured to couple to the second rotary output on a tool driver of a robotic arm. As such, when the second rotary output is activated, the coupling between the second rotary input coupling 230b and the second rotary input cause the roll shaft 245 to rotate about its longitudinal axis. The roll shaft 245 is coupled to a proximal end of the elongate shaft 224 via a roll pulley assembly 295 including a belt 296 that extends around the roll shaft 245 and the elongate shaft 224. As such, activation of the second rotary input causes the roll shaft 245 to rotate thereby activating the roll pulley assembly 295 to rotate the elongate shaft (e.g., along a longitudinal axis of the elongate shaft). The opposed jaws are coupled to a distal end of the elongate shaft 224 and are also caused to rotate about the longitudinal axis of the elongate shaft 224 when the elongate shaft is caused to rotate. As such, activation of the second rotary input causes rotation of the end effector and/or opposed jaws.

As shown in FIG. 10, some implementations of the roll assembly 244 can include a belt tensioner 297 that applies a force against a part of the belt 296 such that the belt 296 has a desired tension. In addition, the belt 296 can include extruded features that are configured to engage surface features along the roll shaft and/or elongate shaft. The belt tensioner 297 and engaging features between the belt and shafts (roll shaft and elongate shaft) can assist with ensuring the belt 296 does not slip when either shaft rotates, as well as keep timing of the position of the end effector relative to the elongate shaft. For example, if the belt was to slip, the operating system may not be aware of such slip and would thus not know the exact position of the end effector relative to the elongate shaft.

FIG. 11 illustrates another embodiment of a tool assembly 300 showing a housing 322 having two rotary input couplings and four linear input couplings. Similar to as described above with respect to the tool assembly 200 of FIG. 4, the rotary input couplings are each configured to couple to a rotary output, such as a rotary actuation motor of a tool driver, and the linear input couplings are each configured to couple to a linear output, such as a linear actuation motor of the tool driver. The interface or coupling either between a rotary input coupling and a rotary output or between a linear input coupling and a linear output can include any number of a variety of couplings, all of which are within the scope of this disclosure.

As shown in FIG. 11, the tool assembly 300 can include a housing 322 with an elongate shaft 324 extending therefrom and an end effector 326 positioned at a distal end of the elongate shaft 324. The elongate shaft 324 can include opposing jaws 329 that are caused to pivot between an open and a closed configuration, as will be described in greater detail below.

FIG. 12 illustrates a part of the housing and shows first and second rotary input couplings 330a, 330b that are configured to couple to first and second rotary outputs, respectively. The first rotary input coupling 330a is mechanically coupled to a transmission shaft 340 such that when the first rotary input coupling 330a is caused to rotate by the first rotary output, the transmission shaft rotates. As will be discussed in greater detail below, the transmission shaft can be configured to assist with controlling and/or activing at least one mechanism of the tool assembly 300, such as a roll assembly (e.g., causes rotation of the end effector 326 alone or in combo with the shaft 340) and a firing assembly (e.g., causes translation of I-beam through the jaws 329).

Furthermore, the second rotary input coupling 330b can be mechanically coupled to a clamping assembly such that when the second rotary input coupling 330b is caused to rotate by the second rotary output, the clamping assembly is activated thereby causing the opposed jaws 329 to open or close, as will be described in greater detail below.

The housing 322 can further include four linear input couplings that are each configured to couple to four linear outputs. For example, first and second linear input couplings 332a, 332b can be a part of an articulation assembly such that, when caused to translate as a result of actuation of first and second linear outputs, articulation of the end effector relative to the elongate shaft is achieved. Furthermore, third and fourth linear input couplings 332c, 332d can also be a part of the articulation assembly and, when caused to translate as a result of actuation of third and fourth linear outputs, are also configured to control articulation of the end effector 326 relative to the elongate shaft 324. For example, activation of the first and second linear inputs can cause the end effector 326 to articulate in a first direction and actuation of the third and fourth linear inputs can cause the end effector 326 to articulate in a second direction (e.g., opposite the first direction).

FIGS. 13-14 illustrate an embodiment of a clamping assembly 346 and a movable rack assembly 351 that controls activation of a roll assembly 344 and a firing assembly 380 of the tool assembly 300. As mentioned above, the clamping assembly 346 can be controlled by the second rotary input for opening and closing the opposed jaws 329 of the end effector 326.

As shown in FIG. 14, the clamping assembly 346 can include the second rotary input coupling 330b that is configured to couple to the second rotary output. The second rotary input coupling 330b can be positioned at a distal end of a closure rotary shaft 331 of the clamping assembly 346. A first closure gear 333 can be positioned along the closure rotary shaft 331 and can be caused to rotate when the closure rotary shaft 331 rotates. As such, activation of the second rotary input can cause rotation of the closure rotary shaft 331 and the first closure gear 333.

The first closure gear 333 can be coupled to a clamping gear train 335, as shown in FIG. 14, which includes a second closure gear 362 coupled to a closure tube 352 that is configured to control the opening and closing of the jaws 329. The second closure gear 362 can include a thru-hole 364 with inner threads that engage outer threads 366 along a part of the closure tube 352. Rotation of the second closure gear 362 can cause translation of the closure tube 352, such as in a distal direction thereby closing the jaws 329, or in a proximal direction thereby opening the jaws 329. When the closure tube 352 is in a distal position, the opposed jaws 329 can be in a closed configuration, and when the closure tube 352 is in a proximal position, the opposed jaws 329 can be in an open configuration. Activation of the second rotary input can directly cause the jaws to open and close and may not be dependent on a position of the transmission shaft 340, which is activated by a first rotary input. As such, in this configuration, the jaws 329 can be opened or closed at any time.

As shown in FIG. 13, the rack assembly 351 can include a first rack connector 339 that connects the rack assembly 351 to the closure tube 352. The first rack connector 339 can be configured such that movement of the closure tube 352 causes the rack assembly 351 to move. For example, the first rack connector 339 can extend between the transmission shaft 340 and the closure tube 352 such that when the closure tube linearly translates in a direction, the transmission shaft linearly translates in the same direction.

The rack assembly 351 can further include a first rack part 311 and a second rack part 313 positioned along the transmission shaft 340. A roll actuator 315 and a firing actuator 317 can also be positioned along the transmission shaft 340 and between the first rack part 311 and the second rack part 313. The first rack part 311 and the second rack part 313 can be coupled to the transmission shaft 340 such that rotation and translation of the transmission shaft can cause rotation and translation, respectively, of the first rack part 311 and the second rack part 313. The roll actuator 315 and a firing actuator 317 can be slidably disposed on the transmission shaft 340 such that translation of the transmission shaft 340 and/or rack assembly 351 does not cause the roll actuator 315 and/or the firing actuator 317 to translate. For example, the roll actuator 315 and firing actuator 317 can be translationally fixed relative to the housing of the tool assembly 300.

Figure 15:
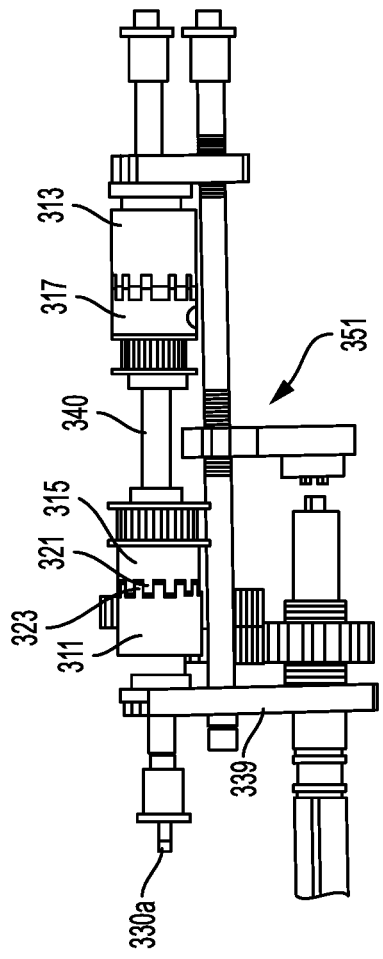
FIG. 15 is a side view of the rack assembly of FIG. 13 in a first position where the roll assembly is engaged for activation by a first rotary input for causing rotation of the elongate shaft and end effector.

As shown in FIG. 15, the roll actuator 315 can be positioned adjacent the first rack part 311 and can include roll engagement features 321 that are configured to mate with first coupling features 323 of the first rack part 311. The roll engagement features 321 and first coupling features 323 can include teeth members that interlock each other and allow rotational torque to be transferred from the first rack part 311 to the roll actuator 315 thereby causing the roll actuator 315 to rotate about and along with the transmission shaft 340. As such, activation of the first rotary input when the rack assembly 351 is in the first position (e.g., the first rack part 311 is coupled to the roll actuator 315) can cause the roll actuator 315 to rotate thereby activing the roll assembly 344 and causing the elongate shaft and end effector to rotate, as will be described in greater detail below.

Figure 16:
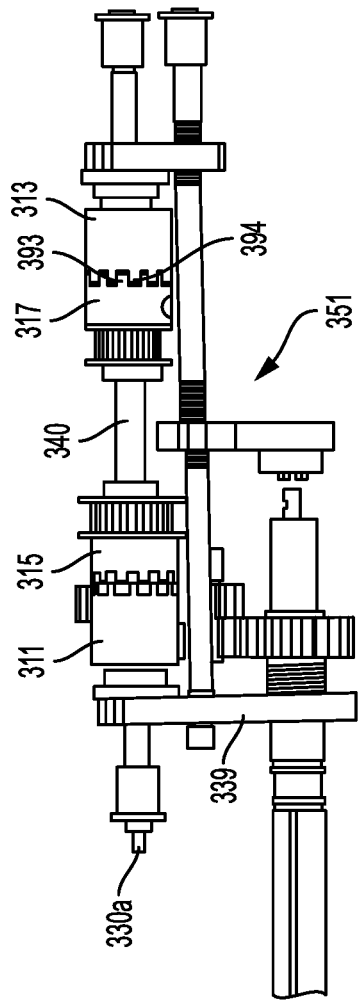
FIG. 16 is a side view of the rack assembly of FIG. 13 in a second position where the firing assembly is engaged for activation by the first rotary input for causing translation of an I-beam through the end effector.

As shown in FIG. 16, the firing actuator 317 can be positioned adjacent the second rack part 313 and can include firing engagement features 393 that are configured to mate with second coupling features 394 of the second rack part 313. The firing engagement features 393 and second coupling features 394 can include teeth members that interlock together and allow rotational torque to be transferred from the second rack part 313 to the firing actuator 315 thereby causing the firing actuator 315 to rotate. As such, activation of the first rotary input when the rack assembly 351 is in the second position (e.g., the second rack part 313 is coupled to the firing actuator 317) can cause the firing actuator 317 to rotate thereby activing the firing assembly 380 and causing the I-beam to travel through the end effector, as will be described in greater detail below.

Figure 17:
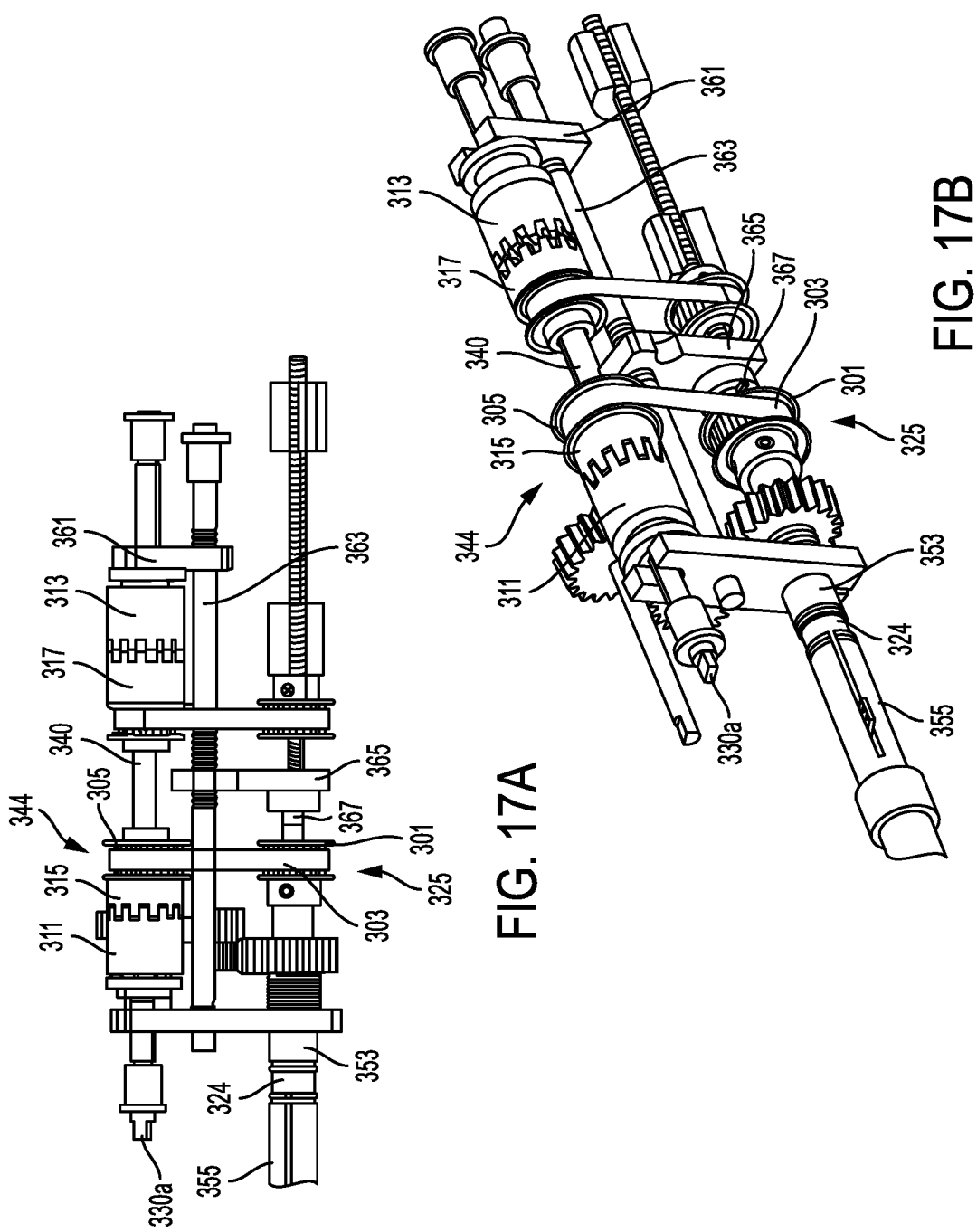
FIG. 17A is a side view of the rack assembly of FIG. 13 in the first position and showing the roll assembly that controls rotation of the end effector and elongate shaft.
FIG. 17B is a side perspective view of the rack assembly of FIG. 17A.

FIGS. 17A-17B show the rack assembly in the first position with the roll assembly 344 engaged with the transmission shaft 340 via the coupling between the roll actuator 315 and the first rack part 311. The roll assembly 344 can include a roll pulley assembly 325 that includes a first pulley 305 along the roll actuator 315 that rotates when the roll actuator 315 is rotated. The roll pulley assembly 325 can further include a second pulley 301 that is coupled to a proximal end of the elongate shaft 324 such that rotation of the second pulley 301 causes rotation of the elongate shaft 324. A roll belt 303 can extend between the first and second pulleys such that rotation of the roll actuator 315 and first pulley 305 causes rotation of the second pulley 301 thereby causing the elongate shaft 324 and the end effector positioned at the distal end of the elongate shaft to rotate. As such, when the rack assembly 351 is in the first position and the first rotary input is activated, the elongate shaft and end effector rotate.

In some embodiments, the elongate shaft 324 can be coupled to a distal part 355 of the closure tube such that rotation of the elongate shaft 324 causes rotation of the distal part 355 of the closure tube. The distal part 355 of the closure tube can be coupled to the end effector such that rotation of the closure tube causes rotation of the end effector 326. Furthermore, the distal part of the closure tube can be coupled to a proximal part 353 of the closure tube. The proximal part 353 of the closure tube can include outer threads that engage inner threads along the second closure gear 362 such that rotation of the second closure gear causes translation (and not rotation) of the proximal part 353 of the closure tube. As such, the distal part 355 of the closure tube (and not the proximal part 353 of the closure tube) can be forced to rotate thereby causing the end effector to rotate. Furthermore, both the distal and proximal parts of the closure tube can translate to cause opening or closing of the jaws.

Figure 18:
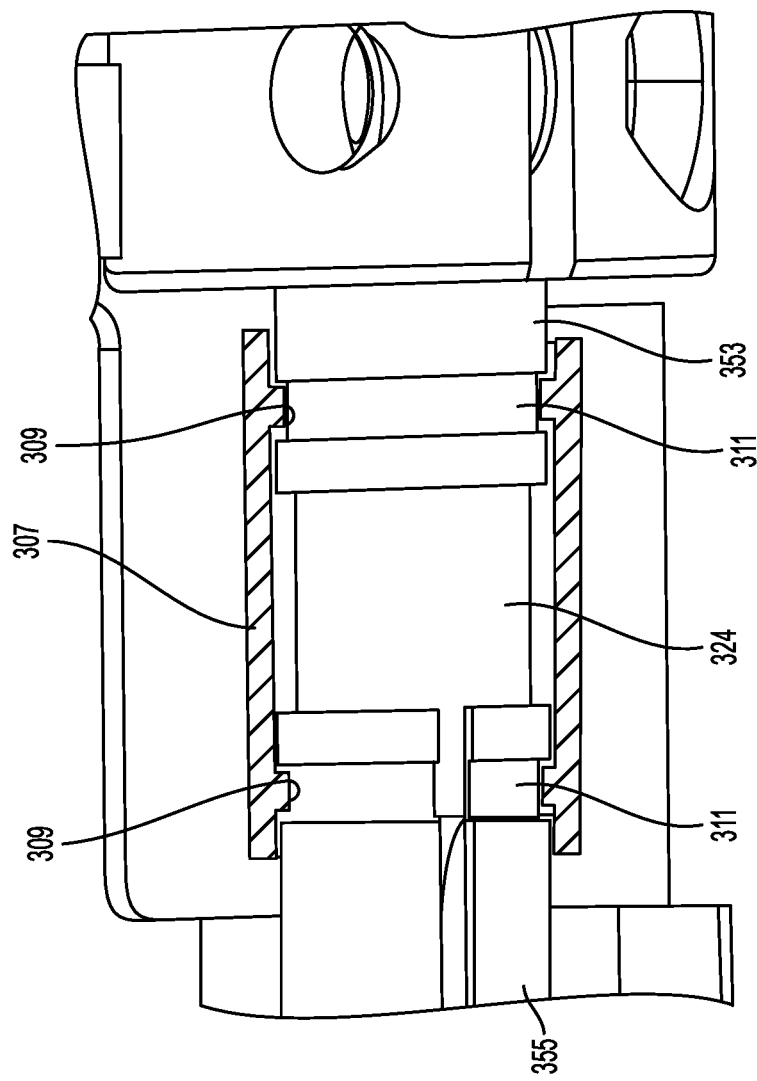
FIG. 18 is a side cross-sectional view of a closure tube coupling of FIG. 17A, showing the coupling between a proximal part of the closure tube and a distal part of the closure tube.

FIG. 18 illustrates a closure tube coupling 307 that couples the proximal part 355 of the closure tube to the distal part 353 of the closure tube. For example, the closure tube coupling 307 can allow rotation of the distal part 355 relative to the proximal part 353, as well as cause simultaneous translation of the proximal and distal parts of the closure tube. As shown in FIG. 18, the closure tube coupling 307 can include proximal and distal coupling features 309 that engage rings 311 along the proximal and distal parts of the closure tube. The proximal and distal coupling features 309 can include extensions that mate with the rings 311 such that the proximal and distal coupling features 309 can slidably rotate along the rings 311. Furthermore, the proximal and distal coupling features 309 can engage the rings 311 such that neither the proximal part nor the distal part of the closure tube can translate relative to each other or the closure tube coupling 307. As such, the closure tube coupling 307 can allow the proximal and distal parts to translate proximally and distally together while allowing the distal part 355 of the closure tube to rotate (e.g., along with rotation of the elongate shaft when the roll assembly is activated) while the proximal part 353 of the closure tube does not rotate.

FIGS. 19 and 20 show an embodiment of a firing assembly 380 engaged with the transmission shaft 340 via the second rack part 317 such that activation of the first rotary input causes activation of the firing assembly 380. The firing assembly 380 can include the firing actuator 317, which can include a first firing pulley 313 of a firing pulley assembly that rotates when the firing actuator 317 is rotated. The firing pulley assembly can further include a second firing pulley 319 that is coupled to a firing rod 382 such that rotation of the second firing pulley 319 can cause translation of the firing rod 382. A roll belt 302 can extend between the first and second firing pulleys such that rotation of the firing actuator 317 and first firing pulley 313 can cause rotation of the second firing pulley 319 thereby causing the firing rod 382 to translate and the I-beam to travel through the end effector. As such, when the rack assembly 351 is in the second position and the second rotary input is activated, the I-beam can translate through the end effector.

In some embodiments, the firing rod 382 can include a rotational coupling 383 that couples a distal part 382a and a proximal part 382b of the firing rod 382 such that the distal and proximal parts 382a, 382b can be forced to translate together and can rotate (or not rotate) independent of each other. For example, the rotational coupling 383 can allow the distal part 382a of the firing rod 382 to rotate relative to the proximal part 382b. As shown in FIG. 19, the proximal part 382b of the firing rod 382 can be coupled to the second firing pulley 319 and can be configured to only translate and not rotate. The rotational coupling 383 can thus allow the I-beam (coupled to the distal part 382a of the firing rod 382) to rotate, such as with the end effector when the roll assembly is activated, while allowing the proximal part 382b to not rotate.

A shown in FIGS. 19 and 20, a rotational lock 385 can be included along the firing rod 382 and can be configured to ensure that the firing rod 382 does not rotate. For example, the firing rod 382 can include at least one flat surface 384 along its length that mates with an inner flat surface 386 of the rotational lock 385. The rotational lock 385 can be prevented from rotating relative to the housing, for example, thereby limiting the firing rod 382 (e.g., the proximal end of the firing rod) to translational movement.

As shown in FIGS. 17A and 17B, the rack assembly can include a rotation locking feature 367 that engages and prevents rotation of the second pulley 301 of the roll assembly 344 thereby preventing the elongate shaft 324 and/or end effector 326 from rotating. The rotation locking feature can engage the second pulley 301 when the rack assembly is in the second position (e.g., during activation of the firing assembly 380). As shown in FIG. 17A, the rack assembly can further include a rack support 363 and a first and second extension 365, 363 that are both coupled to the rack support 363. The second extension 365 can extend between the rotation locking feature 367 and the rack support 363, and the rack support 363 can be coupled to the transmission shaft 340 via the third extension 361. The rack support 363 and second and third extensions 365, 361 can be translationally locked relative to each other such that translation of the transmission shaft causes translation of the rotation locking feature 367. As such, when the transmission shaft and/or rack assembly moves from the first position into the second position, the rotation locking feature 367 moves from a disengaged configuration to an engaged configuration with the second pulley 301 thereby preventing rotation of the elongate shaft and/or end effector. For example, it can be undesirable to have the end effector rotate during cutting of the tissue being grasped by the jaws of the end effector. Such undesirable rotation of the end effector can be prevented with the rotation locking feature 367.

Figure 21:
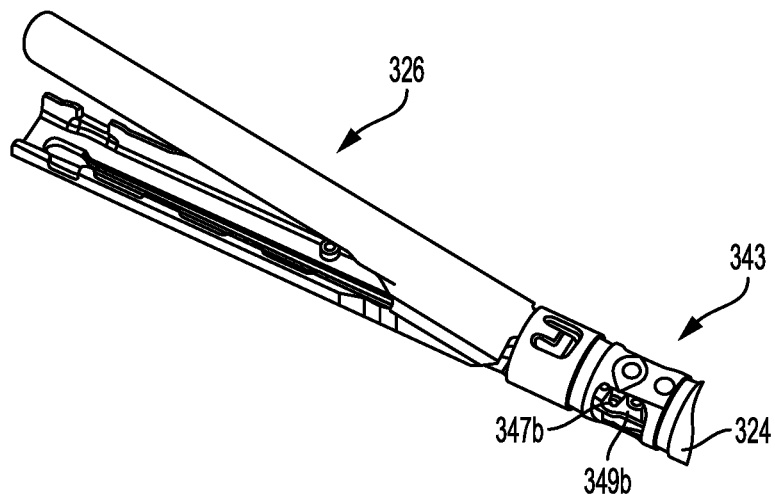
FIG. 21 is a side perspective view of the end effector of FIG. 11 positioned distal to an articulation joint configured to assist with articulating the end effector.
Figure 22:
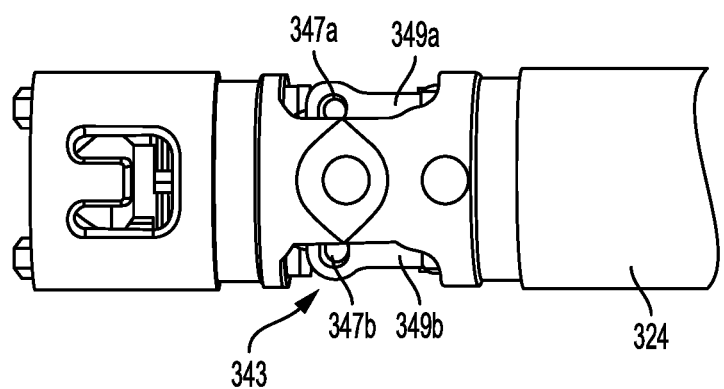
FIG. 22 is a top view of the articulating joint of FIG. 21.

FIGS. 21 and 22 show an articulation joint 343 adjacent the end effector 326 for allowing the end effector 326 to form a variety of angles relative to the longitudinal axis of the elongate shaft 324. The articulation joint 343 can include first and second pivot points 347a, 347b, respectively, that are coupled to first and second articulation beams 349a, 349b, respectively. For example, translation of the first articulation beam 349a and first pivot point 347a in a distal direction can cause the end effector 326 to pivot in a first direction about both the first and second pivot points 347a, 347b. Translation of the second articulation beam 349b and second pivot point 347b in the distal direction can cause the end effector 326 to pivot about both the first and second pivot points 347a, 347b in a second direction. The first and second directions can be in opposite directions from each other.

Figure 23:
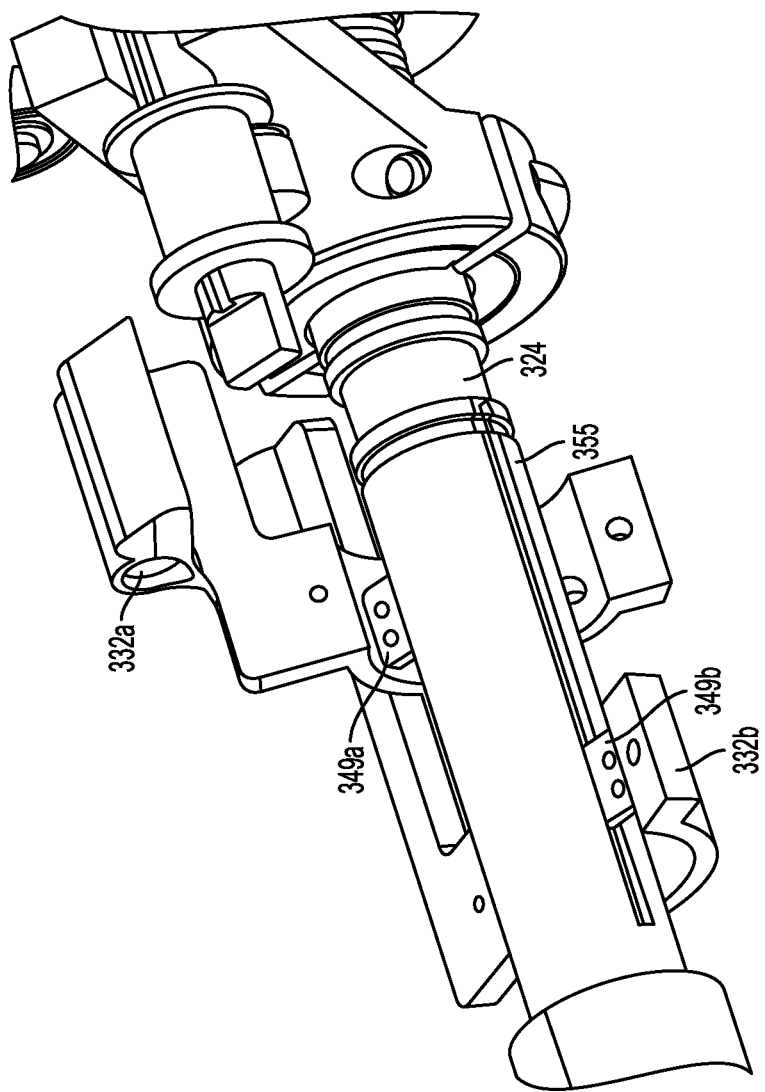
FIG. 23 is a side perspective view of linear input couplings of FIG. 12 that are acted upon by linear inputs for controlling articulation of the end effector.

FIG. 23 shows a first linear input coupling 332a coupled to the first articulation beam 349a and a second linear input coupling 332b coupled to the second articulation beam 349b. Activation of a first linear actuator, which is coupled to the first linear input coupling 332a, can cause the first articulation beam 349a to translate thereby causing the end effector 326 to pivot in the first direction. Similarly, activation of a second linear actuator, which is coupled to the second linear input coupling 332b, can cause the second articulation beam 349b to translate thereby causing the end effector 326 to pivot in the second direction.

In some embodiment, more than one linear actuator can be activated to cause the end effector to pivot in either the first or second direction. For example two linear actuators can be activated to cause the first or second articulation beams 349a, 349b to translate thereby causing the end effector 326 to pivot. Any number of linear actuators can be used to articulate the end effector 326.

Preferably, components of the invention described herein will be processed before use. First, a new or used instrument is obtained and if necessary cleaned. The instrument can then be sterilized. In one sterilization technique, the instrument is placed in a closed and sealed container, such as a plastic or TYVEK bag. The container and instrument are then placed in a field of radiation that can penetrate the container, such as gamma radiation, x-rays, or high energy electrons. The radiation kills bacteria on the instrument and in the container. The sterilized instrument can then be stored in the sterile container. The sealed container keeps the instrument sterile until it is opened in the medical facility.

Typically, the device is sterilized. This can be done by any number of ways known to those skilled in the art including beta or gamma radiation, ethylene oxide, steam, and a liquid bath (e.g., cold soak). An exemplary embodiment of sterilizing a device including internal circuitry is described in more detail in U.S. Pat. No. 8,114,345 filed Feb. 8, 2008 and entitled "System And Method Of Sterilizing An Implantable Medical Device." It is preferred that device, if implanted, is hermetically sealed. This can be done by any number of ways known to those skilled in the art.

One skilled in the art will appreciate further features and advantages of the invention based on the above-described embodiments. Accordingly, the invention is not to be limited by what has been particularly shown and described, except as indicated by the appended claims. All publications and references cited herein are expressly incorporated herein by reference in their entirety.

What is claimed is:

1. A surgical tool, comprising:
   a housing;
   an elongate shaft extending distally from the housing and having an end effector with opposed jaws on a distal end thereof; and
   a transmission shaft disposed within the housing and movable between a first position, in which the transmission shaft is configured to be rotated by a rotary input to cause the opposed jaws to move between open and closed positions such that the rotary input is configured to rotate during jaw closure, and a second position, in which the transmission shaft is configured to be rotated by the rotary input to cause at least one of articulation of the end effector and firing of at least one staple from the end effector.

2. The surgical tool of claim 1, wherein the transmission shaft is configured to move between the first position and the second position in response to linear movement of a linear input.

3. The surgical tool of claim 1, wherein the transmission shaft couples to a first coupling feature when in the first position to thereby allow rotation of the transmission shaft to actuate a clamping assembly, actuation of the clamping assembly causing the opposed jaws to move between the open and closed positions.

4. The surgical tool of claim 3, wherein the transmission shaft uncouples from the first coupling feature and couples to a second coupling feature when in the second position to thereby allow rotation of the transmission shaft to cause at least one of articulation of the end effector and firing of at least one staple from the end effector.

5. The surgical tool of claim 4, further comprising a shifter coupled to the transmission shaft and configured to be translated by a linear input to effect linear translation of the transmission shaft between the first position and the second position.

6. The surgical tool of claim 3, wherein the clamping assembly is coupled between the transmission shaft and the end effector, the clamping assembly including a closure tube configured to translate longitudinally along the elongate shaft to open and close the jaws when the transmission shaft is rotated in the first position.

7. The surgical tool of claim 6, wherein the clamping assembly comprises:
  a first gear disposed along the transmission shaft and configured to rotate with the transmission shaft when the transmission shaft is in the first position; and
  a second gear engaged with the first gear such that the second gear rotates when the first gear rotates, the second gear including a thru-hole having inner threads that engage outer threads on a proximal end of the closure tube thereby translating the closure tube when the second gear rotates.

8. The surgical tool of claim 4, further comprising a firing assembly coupled between the transmission shaft and the end effector, the firing assembly including a knife assembly configured to translate longitudinally through the opposed jaws when the transmission shaft is rotated in the second position.

9. The surgical tool of claim 8, wherein the firing assembly comprises:
  a worm gear disposed along the transmission shaft and configured to rotate with the transmission shaft when the transmission shaft is in the second position;
  a pinion gear coupled to the worm gear such that rotation of the worm gear causes the pinion gear to rotate;
  a rack that is longitudinally translatable relative to the housing to cause corresponding longitudinal translation of the knife assembly through the opposed jaws; and
  a crossover gear that is coupled between the pinion gear and the rack such that the crossover gear rotates as a result of the pinion gear rotating thereby causing longitudinal translation of the rack.

10. The surgical tool of claim 9, wherein the crossover gear is movable between an extended position, in which it is engaged with the rack, and a collapsed position, in which it is moved out of engagement with the rack.

11. The surgical tool of claim 10, further comprising a bailout lever configured to move the crossover gear from the extended position to the collapsed position.

12. The surgical tool of claim 11, wherein the bailout lever includes a ratchet feature that engages the rack such that movement of the lever is effective to cause proximal longitudinal translation of the rack.

13. The surgical tool of claim 1, further comprising a roll assembly configured to rotate the end effector about a longitudinal axis of the transmission shaft, the roll assembly including a pulley configured to be rotated relative to the housing by a third actuation component, the pulley being coupled to the transmission shaft such that rotation of the pulley effects rotation of the transmission shaft.

14. The surgical tool of claim 1, further comprising:
  a worm gear disposed along the transmission shaft and configured to rotate with the transmission shaft when the transmission shaft is in the second position; and
  a pinion gear coupled to the worm gear such that rotation of the worm gear causes the pinion gear to rotate.

15. The surgical tool of claim 1, wherein the transmission shaft is biased to the first position by a transmission biasing member.

16. The surgical tool of claim 1, wherein the surgical tool comprises a robotic surgical tool.

17. A surgical tool, comprising:
  a housing;
  an elongate shaft extending distally from the housing and having an end effector with opposed jaws on a distal end thereof, the end effector being configured to seal and transect tissue grasped between the opposed jaws; and
  an actuation assembly configured to move between first and second positions, the actuation assembly configured to open and close the opposed jaws in the first position upon receiving a rotary drive force such that the rotary drive force is configured to be applied during opening and closing of the opposed jaws, and the actuation assembly configured to actuate a second function in the end effector in the second position upon receiving the rotary drive force.

18. The surgical tool of claim 17, wherein the second function in the end effector is one of articulating the end effector or causing the end effector to seal and transect tissue grasped between the opposed jaws.

19. The surgical tool of claim 17, wherein the actuation assembly is configured to move between the first position and the second position in response to linear movement of a linear input.

20. The surgical tool of claim 17, wherein the actuation assembly couples to a first coupling feature when in the first position to thereby allow rotation of the actuation assembly to actuate a clamping assembly to cause the opposed jaws to open and close.

21. The surgical tool of claim 17, wherein the actuation assembly is biased to the first position.

22. The surgical tool of claim 17, further comprising a shifter coupled to the actuation assembly and configured to cause the actuation assembly to move between the first and second positions.

23. The surgical tool of claim 22, wherein the shifter is configured to be translated by a linear input to effect linear translation of the actuation assembly between the first and second positions.

24. The surgical tool of claim 14, further comprising:
  a rack that is longitudinally translatable relative to the housing to cause corresponding longitudinal translation of a knife assembly through the opposed jaws; and
  a crossover gear that is coupled between the pinion gear and the rack such that the crossover gear rotates as a result of the pinion gear rotating thereby causing longitudinal translation of the rack.

25. The surgical tool of claim 17, further comprising:
a worm gear disposed along the actuation assembly and configured to rotate with the actuation assembly when the actuation assembly is in the second position upon receiving the rotary drive force;
a pinion gear coupled to the worm gear such that rotation of the worm gear causes the pinion gear to rotate;
a rack that is longitudinally translatable relative to the housing to cause corresponding longitudinal translation of a knife assembly through the opposed jaws; and
a crossover gear that is coupled between the pinion gear and the rack such that the crossover gear rotates as a result of the pinion gear rotating thereby causing longitudinal translation of the rack.

26. The surgical tool of claim 15, wherein the transmission shaft is configured to move between the first position and the second position in response to linear movement of a linear input against the transmission biasing member.

\* \* \* \* \*